US009457073B2

United States Patent
Kikkert et al.

(10) Patent No.: US 9,457,073 B2
(45) Date of Patent: Oct. 4, 2016

(54) LIVE ATTENUATED REPLICATION-COMPETENT ARTERIVIRUSES HAVING DECREASED DUB/DEISGYLATING ACTIVITY

(71) Applicants: Leiden University Medical Center, Leiden (NL); University of Manitoba, Winnipeg (CA)

(72) Inventors: Marjolein Kikkert, Sassenheim (NL); Brian Leonard Mark, Winnipeg (CA); Puck Bertyne van Kasteren, Bussum (NL); Terrence William James, Grande Pointe (CA); Eric John Snijder, Bodegraven (NL)

(73) Assignee: University of Manitoba, Winnipeg (CA)

( * ) Notice: Subject to any disclaimer, the term of this patent is extended or adjusted under 35 U.S.C. 154(b) by 18 days.

(21) Appl. No.: 14/035,415

(22) Filed: Sep. 24, 2013

(65) Prior Publication Data

US 2014/0154265 A1    Jun. 5, 2014

(30) Foreign Application Priority Data

Sep. 26, 2012  (EP) .................................... 12186162

(51) Int. Cl.
| | |
|---|---|
| A61K 39/12 | (2006.01) |
| A61K 39/42 | (2006.01) |
| A61K 9/02 | (2006.01) |
| C12N 7/00 | (2006.01) |
| A61K 39/02 | (2006.01) |
| A61K 39/40 | (2006.01) |
| A61K 39/00 | (2006.01) |

(52) U.S. Cl.
CPC .............. *A61K 39/12* (2013.01); *A61K 39/02* (2013.01); *A61K 39/40* (2013.01); *A61K 39/42* (2013.01); *C12N 7/00* (2013.01); *A61K 2039/5254* (2013.01); *A61K 2039/552* (2013.01); *C07K 2299/00* (2013.01); *C12N 2770/10021* (2013.01); *C12N 2770/10034* (2013.01); *C12N 2770/10062* (2013.01)

(58) Field of Classification Search
None
See application file for complete search history.

(56) References Cited

U.S. PATENT DOCUMENTS

| | | |
|---|---|---|
| 2011/0033498 A1 | 2/2011 | Garcia-Sastre et al. |
| 2012/0213810 A1 | 8/2012 | Burgard et al. |
| 2014/0154265 A1* | 6/2014 | Kikkert et al. ............ 424/159.1 |

FOREIGN PATENT DOCUMENTS

| | | |
|---|---|---|
| WO | 2009/008924 A3 | 1/2009 |
| WO | 2012/063212 A1 | 5/2012 |

OTHER PUBLICATIONS van Kasteren et al. (PNAS; published online Feb. 2013 at www.pnas.org/cgi/doi/10.1073/pnas.1218464110: E838-E847).*
van Kasteren et al. (Veterinary Microbiology. Jul. 2015; 178: 132-137).*
Sequence from Database UniProt Jul. 5, 2004 Access No. Q6TXK6_PRRSV by Fang et al.*
Akutsu et al., "Molecular basis for ubiquitin and ISG15 cross-reactivity in viral ovarian tumor domains", Proceedings of the National Academy of Sciences USA, 2011, pp. 2228-2233, vol. 108(6).
Arguello et al., "Ub Surpised: Viral Ovarian Tumor Domain Proteases Remove Ubiquitin and ISG-15 Conjugates", Cell Host & Microbe, 2007, pp. 367-369.
Balasuriya et al., "Development and characterization of an infectious cDNA clone of the virulent Bucyrus strain of Equine arteritis virus", Journal of General Virology, 2007, pp. 918-924, vol. 88.
Capodagli et al., "Structural Analysis of a viral Ovarian Tumor Domain Protease from the Crimean-Congo Hemorrhagic Fever Virus in Complex with Covalently Bonded Ubiquitin", Journal of Virology, 2011, pp. 3621-3630, vol. 85(7).
Dikic et al., "Ubiquitin-binding domains—from structures to functions", Molecular Cell Biology, 2009, pp. 659-671, vol. 10.
Frias-Staheli et al., "Ovarian Tumor Domain-Containing Viral Proteases Evade Ubiquitin—and ISG 15-Dependent Innate Immune Responses", Cell Host & Microbe, 2007, pp. 404-416.
Fang et al., "Heterogeneity in Nsp2 of European-like porcine reproductive and respiratory syndrome viruses isolated in the United States", Virus Research, 2004, pp. 229-235, vol. 100.
Han et al., "The Porcine Reproductive and Respiratory Syndrome Virus nsp2 Cysteine Protease Domain Possesses both trans- and cis-Cleavage Activities", Journal of Virology, 2009, pp. 9449-9463, vol. 83(18).
Huang et al., "Phosphorylation-dependent activity of the deubiquitinase DUBA", Nature Structural & Molecular Biology, 2012, pp. 171-176, vol. 19(2).
James et al., "Structural basis for the removal of ubiquitin and interferon-stimulated gene 15 by a viral ovarian tumor domain-containing protease", Proceedings of the National Academy of Sciences USA, 2011, pp. 2222-2227, vol. 108(6).
James et al., Supporting Information, found at http://www.pnas.org/cgi/doi/10.1073/pnas.1013388108, 2011, 5 pages.
Jiang et al., "The role of ubiquitylation in immune defence and pathogen evasion", Nature Reviews Immunology, 2012, pp. 35-48, vol. 12.
Kikkert et al., CS17-5—Arteri- and nairovirus OTU domain-containing proteases target ubiquitin-regulated factors in the RLR-mediated innate immune signaling pathway, Cytokine, 2011, pp. 108, vol. 56 (Abstract).
Leng et al., "Mutations in the genome of the highly pathogenic porcine reproductive and respiratory syndrome virus potentially related to attenuation", Veterinary Microbiology, 2012, pp. 50-60, vol. 157.

(Continued)

*Primary Examiner* — Shanon A Foley

(57) ABSTRACT

The present invention relates to replication-competent Arteriviruses having a decreased DUB/deISGylating activity due to a mutation in the PLP2 domain of the non-structural protein nsp2, to their use as a medicament, their use as a vaccine and in prophylaxis, to vaccines comprising such Arteriviruses and to Arteriviral PLP2-ubiquitin complexes.

6 Claims, 10 Drawing Sheets

(56) References Cited

OTHER PUBLICATIONS

Figure 1:
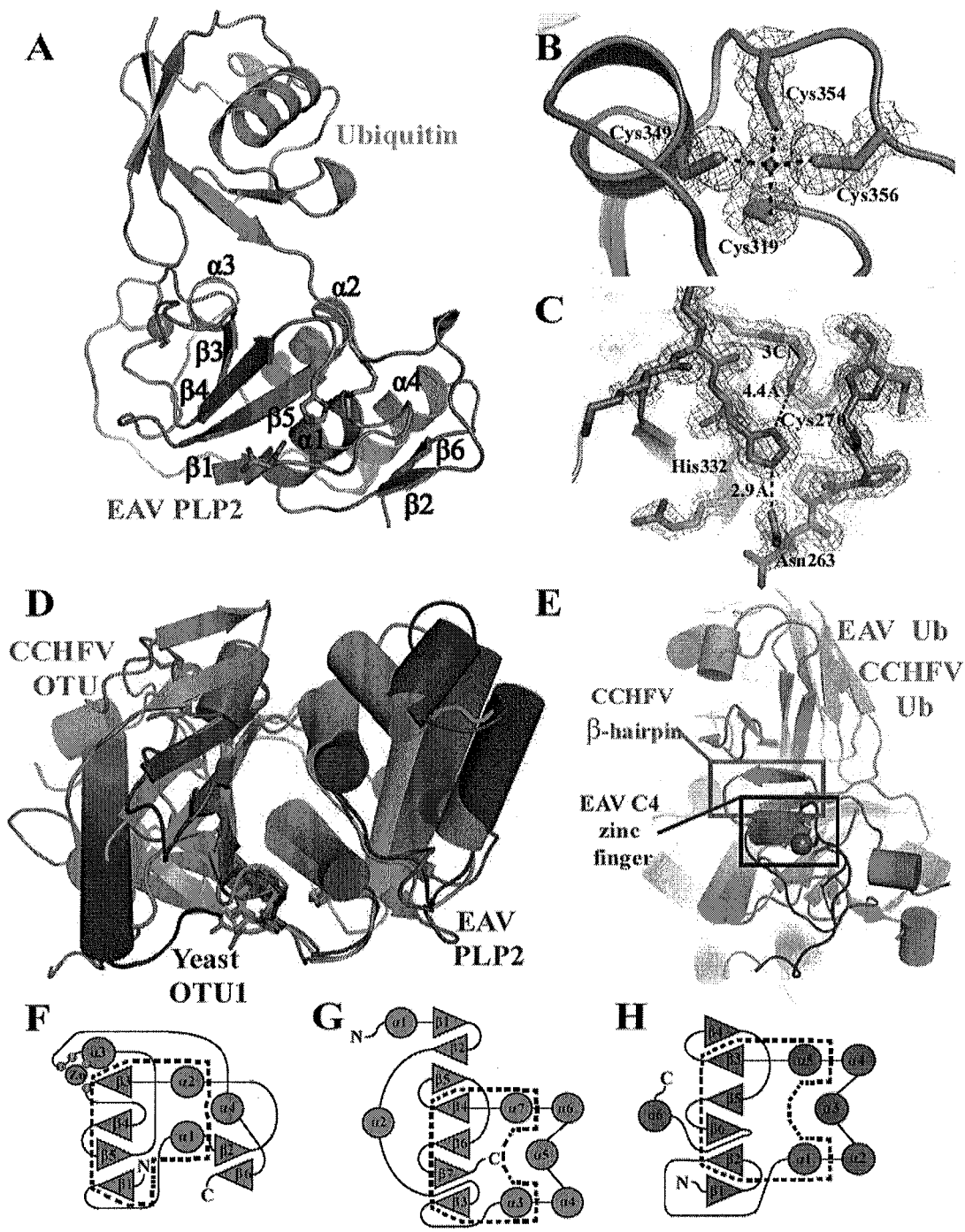

Luo et al., "Porcine reproductive and respiratory syndrome virus (PRRSV) suppresses interferon-β production by interfering with the RIG-1 signaling pathway", Molecular Immunology, 2008, pp. 2839-2846, vol. 45.

Messick et al., "Structural Basis for Ubiquitin Recognition by the Otu1 Ovarian Tumor Domain Protein", The Journal of Biological Chemistry, 2008, pp. 11038-11049, vol. 283(16).

Sun et al., "The cysteine protease domain of PRRSV nonstructural protein 2 possesses deubiquitinating and interferon antagonism functions", Dec. 3-4, 2010 International PPRS Symposium Final Program, Chicago, IL, 2 Pages.

Sun et al., "ISG15 and PRRSV nsp2 OTU domain mediated delSGylation function", Dec. 2-3, 2011 International PPRS Symposium Final Program, Chicago, IL, 3 Pages.

Sun et al., "Coronavirus Papain-like Proteases Negatively Regulate Antiviral Innate Immune Response through Disruption of STING-Mediated Signaling", PLOS One, 2012, e30802, pp. 1-11, vol. 7, Issue 2.

Sun et al., "Nonstructural Protein 2 of Porcine Reproductive and Respiratory Syndrome Virus Inhibits the Antiviral Function of Interferon-Stimulated Gene 15", Journal of Virology, 2012, pp. 3839-3850.

Sun et al., "The Cysteine Protease Domain of Porcine Reproductive and Respiratory Syndrome Virus Nonstructural Protein 2 Possesses Deubiquitinating and Interferon Antagonism Functions", Journal of Virology, 2010, pp. 7832-7846, vol. 84(15).

van Kasteren et al., "Arterivirus and Nairovirus Ovarian Tumor Domain-Containing Deubiquitinases Target Activated RIG-1 to Control Innate Immune Signaling", Journal of Virology, pp. 773-785, vol. 86(2), 2012.

Wang et al., "Enhancing neutralizing antibody production by an interferon-inducing porcine reproductive and respiratory syndrome virus strain", Vaccine, 2013, pp. 5537-5543, vol. 31.

Yu et al., "New genomic characteristics of highly pathogenic porcine reproducgtive and respiratory syndrome viruses do not lead to significant changes in pathogenicity", Veterinary Microbiology, 2012, pp. 291-299, vol. 158.

Zhang et al., "Molecular epidemiology and genetic characterization of equine arteritis virus isolates associated with the 2006-2007 multi-state disease occurrence in the USA", Journal of General Virology, 2010, pp. 2286-2301, vol. 91.

Zhou et al., "Complete Genome Sequence of Two Novel Chinese Virulent Porcine Reproductive and Respiratory Syndrome Virus Variants", Journal of Virology, 2012, pp. 6373-6374, vol. 86(11).

European Patent Register, About this file: WO2009008924, found at https://register.epo.org/espacenet/application?number=EP08826151, 2 pages, dated Jan. 25, 2012.

Partial European Search Report for EP Application No. 12186162.9, dated Feb. 28, 2013.

European Search Report for EP Application No. 12186162.9, dated Jun. 18, 2013.

* cited by examiner

Multiple sequence alignment of EAV and PRRSV sequences made using ClustalW in Geneious (alignments used to make the comparative molecular models of Lelystad and VR-2332)

```
                                                      |    |    |    |    |    |    |
EAV Bucyrus PLP2 X-ray structure NC_002532   261 GYNPPGDGACGYRCLAFMNG--------ATVVSAGCSSDLWCDDELAYRVFQLSPTFTVT 312
PRRSV Lelystad nsp2 (aa 420-555) M96262      420 TYSPPTDGSCGWHVLAAIMNRMINGDFTSPLTQYNRPEDDWASDYDLVQAIQCLR-LPAT 478
PRRSV VR-2332 nsp2 (aa 428-566)  U87392      428 HYSPPAEGNCGWHCISAIANRMVNSKFETTLPERVRPPDDWATDEDLVNAIQILR-LPAA 486
PRRSV GM2 nsp2 (aa 428-566)      JN662424    428 SYSPPADGNCGWHCISAIANRMVNSDFKTTLPERVRPPDDWATDEDLVNTIQVLK-LPAA 486
                                                           *

EAV Bucyrus PLP2 X-ray structure NC_002532   313 IPGGRVcPNAKYAMICDKQHWRVKRAKGVG-LCLDESCFRGIcNcQRMSGPP----PAPV 367
PRRSV Lelystad nsp2 (aa 420-555) M96262      479 VVRNRAcPNAKYLIKLNGVHWEVEVRSGMAPRSLSRECVVGVcS-EGCVAPP--YPADGL 535
PRRSV VR-2332 nsp2 (aa 428-566)  U87392      487 LDRNGAcTSAKYVLKLEGEHWTVTVTPGMSPSLLPLECVQGCcGHKGGLGSPDAVEVSGF 546
PRRSV GM2 nsp2 (aa 428-566)      JN662424    487 LDRNGAcGSAKYVLKLEGEHWTVSVAPGMSPYLLPLECVQGCcEHKGGLVSPDAVEVSGF 546

EAV Bucyrus PLP2 X-ray structure NC_002532   368 SAAVLDHILEAATFGNVRVV 387
PRRSV Lelystad nsp2 (aa 420-555) M96262      536 PKRALEALASAYRLPSDCVS 555
PRRSV VR-2332 nsp2 (aa 428-566)  U87392      547 DPACLDRLAEVMHLPSSAIP 566
PRRSV GM2 nsp2 (aa 428-566)      JN662424    547 DPACLDRLAKVMHLPSSTIP 566
```

Legend

Residue numbering based on EAV sequence

* - Denotes active site cysteine

*Italicized residues* - Part of of the ubiquitin interaction surface

Underlined residues - Part of of the ubiquitin interaction surface, including an identified hydrogen bond or salt bridge with ubiquitin according to the EAV PLP2 crystal structure. Note: some of the hydrogen bonds occur between the backbone amide or carbonyl oxygen of these residue, thus the side chain can be different between viral PLP2s, yet the interaction remains intact (eg. EAV PLP2: S290, R317, possibly Gln331).

Boxed residues (dashed box) are those that are near the PLP2 active site and interact with the C-terminal RLRGG motif of ubiquitin. Mutating these residues could affect polyprotein processing.

Boxed residues (solid box) are those that bind to the beta-grasp fold of Ub (ie. the main body of Ub), not near the active site, and together form the ubiquitin interaction surface (shown as a surface on PLP2 in Figure 1). Note, the cysteine residues comprising the zinc-binding site reside near residues that bind the beta-grasp fold of ubiquitin and thus the zinc-binding site appears intimately involved in Ub-binding.

Lower case cysteine residues (c) - zinc-binding site cysteine (based on EAV PLP2 crystal structure)

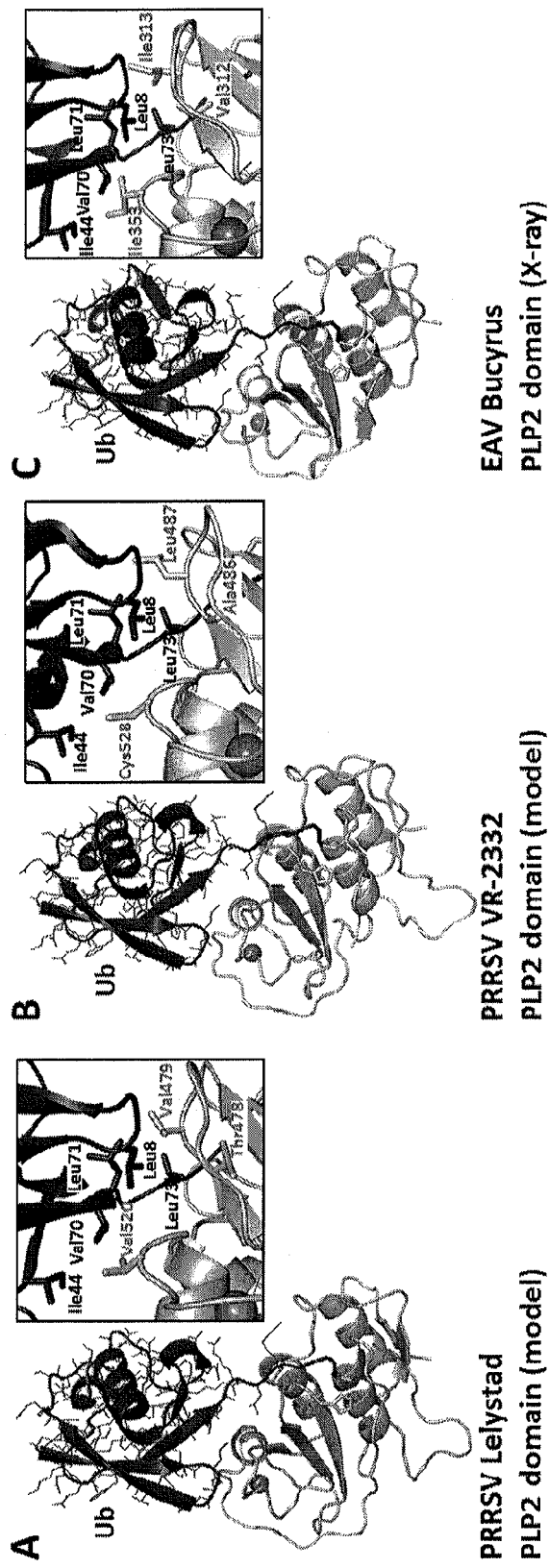
Figures 4 A, B and C

Residues of PRRSV PLP2 domains predicted to bind Ub based on structure/function studies of the EAV PLP2 domain

| PLP2 domain: | PRRSV (Lelystad) | PRRSV (VR-2332) | EAV (Bucyrus) |
| --- | --- | --- | --- |
| Functionally homologous Residues: | Thr 478 | Ala 486 | Thr 312 |
| | Val 479 | Leu 487 | Ile 313 |
| | Val 520 | Cys 528 | Ile 353 |

Figure 4D

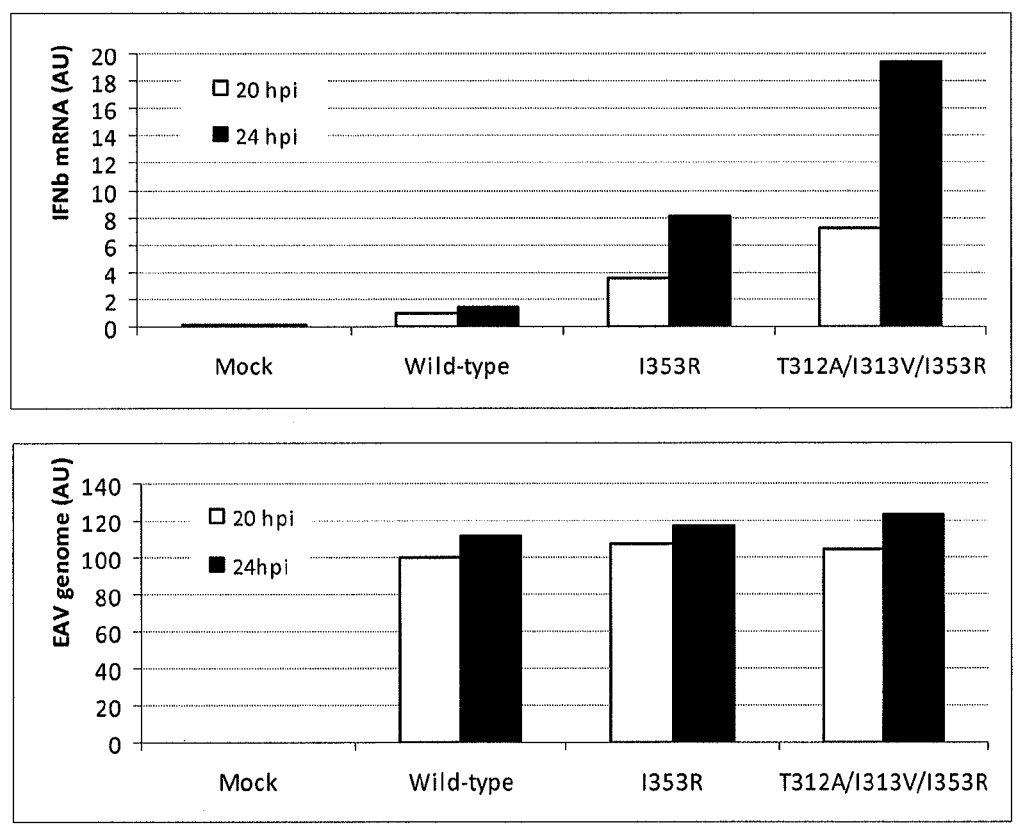
Figure 9A (top), 9B (bottom).

SEQUENCE LISTING

<160> NUMBER OF SEQ ID NOS: 27

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
tgccgcctgg agaaagctgc					20

<210> SEQ ID NO 2
<211> LENGTH: 20
<212> TYPE: DNA
<213> ORGANISM: artificial sequence -continued

```
<220> FEATURE:
<223> OTHER INFORMATION: primer

<400> SEQUENCE: 2
gagggcaatg ccagccccag                                                       20

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
ccacgccatc ctgcgtctgg                                                       20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
accgctcgtt gccgatggtg                                                       20

<210> SEQ ID NO 5
<211> LENGTH: 22
<212> TYPE: DNA
<213> ORGANISM: artificial sequence
<220> FEATURE:
<223> OTHER INFORMATION: primer

<400> SEQUENCE: 5
aggtggatcc tcccaatggc cc                                                    22

<210> SEQ ID NO 6
<211> LENGTH: 20
<212> TYPE: DNA
<213> ORGANISM: artificial sequence
<220> FEATURE:
<223> OTHER INFORMATION: primer

<400> SEQUENCE: 6
ggggcaacgt tgaggggctc                                                       20

<210> SEQ ID NO 7
<211> LENGTH: 20
<212> TYPE: DNA
<213> ORGANISM: artificial sequence
<220> FEATURE:
<223> OTHER INFORMATION: primer

<400> SEQUENCE: 7
ccgacccggt gtgaccgttg                                                       20

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8
aagggtcgcg ggtgccaatg                                                       20
```

<210> SEQ ID NO 9
<211> LENGTH: 127
<212> TYPE: PRT
<213> ORGANISM: Equine arteritis virus

<400> SEQUENCE: 9

Gly Tyr Asn Pro Pro Gly Asp Gly Ala Cys Gly Tyr Arg Cys Leu Ala
1               5                   10                  15

Phe Met Asn Gly Ala Thr Val Val Ser Ala Gly Cys Ser Ser Asp Leu
                20                  25                  30

Trp Cys Asp Asp Glu Leu Ala Tyr Arg Val Phe Gln Leu Ser Pro Thr
            35                  40                  45

Phe Thr Val Thr Ile Pro Gly Gly Arg Val Cys Pro Asn Ala Lys Tyr
        50                  55                  60

Ala Met Ile Cys Asp Lys Gln His Trp Arg Val Lys Arg Ala Lys Gly
65                  70                  75                  80

Val Gly Leu Cys Leu Asp Glu Ser Cys Phe Arg Gly Ile Cys Asn Cys
                85                  90                  95

Gln Arg Met Ser Gly Pro Pro Ala Pro Val Ser Ala Ala Val Leu
                100                 105                 110

Asp His Ile Leu Glu Ala Ala Thr Phe Gly Asn Val Arg Val Val
            115                 120                 125

<210> SEQ ID NO 10
<211> LENGTH: 136
<212> TYPE: PRT
<213> ORGANISM: Porcine reproductive and respiratory syndrome virus

<400> SEQUENCE: 10

Thr Tyr Ser Pro Pro Thr Asp Gly Ser Cys Gly Trp His Val Leu Ala
1               5                   10                  15

Ala Ile Met Asn Arg Met Ile Asn Gly Asp Phe Thr Ser Pro Leu Thr
                20                  25                  30

Gln Tyr Asn Arg Pro Glu Asp Asp Trp Ala Ser Asp Tyr Asp Leu Val
            35                  40                  45

Gln Ala Ile Gln Cys Leu Arg Leu Pro Ala Thr Val Val Arg Asn Arg
        50                  55                  60

Ala Cys Pro Asn Ala Lys Tyr Leu Ile Lys Leu Asn Gly Val His Trp
65                  70                  75                  80

Glu Val Glu Val Arg Ser Gly Met Ala Pro Arg Ser Leu Ser Arg Glu
                85                  90                  95

Cys Val Val Gly Val Cys Ser Glu Gly Cys Val Ala Pro Pro Tyr Pro
                100                 105                 110

Ala Asp Gly Leu Pro Lys Arg Ala Leu Glu Ala Leu Ala Ser Ala Tyr
            115                 120                 125

Arg Leu Pro Ser Asp Cys Val Ser
    130                 135

<210> SEQ ID NO 11
<211> LENGTH: 139
<212> TYPE: PRT
<213> ORGANISM: Porcine reproductive and respiratory syndrome virus

<400> SEQUENCE: 11

His Tyr Ser Pro Pro Ala Glu Gly Asn Cys Gly Trp His Cys Ile Ser
1               5                   10                  15

Ala Ile Ala Asn Arg Met Val Asn Ser Lys Phe Glu Thr Thr Leu Pro

-continued

```
                    20                  25                  30
Glu Arg Val Arg Pro Pro Asp Asp Trp Ala Thr Asp Glu Asp Leu Val
                35                  40                  45

Asn Ala Ile Gln Ile Leu Arg Leu Pro Ala Ala Leu Asp Arg Asn Gly
    50                  55                  60

Ala Cys Thr Ser Ala Lys Tyr Val Leu Lys Leu Glu Gly Glu His Trp
65                  70                  75                  80

Thr Val Thr Val Thr Pro Gly Met Ser Pro Ser Leu Leu Pro Leu Glu
                85                  90                  95

Cys Val Gln Gly Cys Cys Gly His Lys Gly Gly Leu Gly Ser Pro Asp
                100                 105                 110

Ala Val Glu Val Ser Gly Phe Asp Pro Ala Cys Leu Asp Arg Leu Ala
            115                 120                 125

Glu Val Met His Leu Pro Ser Ser Ala Ile Pro
        130                 135

<210> SEQ ID NO 12
<211> LENGTH: 139
<212> TYPE: PRT
<213> ORGANISM: Porcine reproductive and respiratory syndrome virus

<400> SEQUENCE: 12

Ser Tyr Ser Pro Pro Ala Asp Gly Asn Cys Gly Trp His Cys Ile Ser
1               5                   10                  15

Ala Ile Ala Asn Arg Met Val Asn Ser Asp Phe Lys Thr Thr Leu Pro
                20                  25                  30

Glu Arg Val Arg Pro Pro Asp Asp Trp Ala Thr Asp Glu Asp Leu Val
                35                  40                  45

Asn Thr Ile Gln Val Leu Lys Leu Pro Ala Ala Leu Asp Arg Asn Gly
    50                  55                  60

Ala Cys Gly Ser Ala Lys Tyr Val Leu Lys Leu Glu Gly Glu His Trp
65                  70                  75                  80

Thr Val Ser Val Ala Pro Gly Met Ser Pro Tyr Leu Leu Pro Leu Glu
                85                  90                  95

Cys Val Gln Gly Cys Cys Glu His Lys Gly Gly Leu Val Ser Pro Asp
                100                 105                 110

Ala Val Glu Val Ser Gly Phe Asp Pro Ala Cys Leu Asp Arg Leu Ala
            115                 120                 125

Lys Val Met His Leu Pro Ser Ser Thr Ile Pro
        130                 135

<210> SEQ ID NO 13
<211> LENGTH: 81
<212> TYPE: PRT
<213> ORGANISM: Equine arteritis virus

<400> SEQUENCE: 13

Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Thr Ile Pro Gly Gly Arg
                20                  25                  30

Val Cys Ser Asn Ala Lys Tyr Ala Met Ile Cys Asp Lys Gln His Met
            35                  40                  45

Arg Val Lys Arg Ala Lys Gly Val Gly Leu Cys Leu Asp Glu Ser Cys
        50                  55                  60

Phe Arg Gly Ile Cys Asn Cys Gln Arg Met Ser Phe Gly Asn Val Arg
```

```
                65                  70                  75                  80
Val

<210> SEQ ID NO 14
<211> LENGTH: 81
<212> TYPE: PRT
<213> ORGANISM: Equine arteritis virus

<400> SEQUENCE: 14

Gly Tyr Asn Pro Pro Gly Asp Gly Ala Ala Gly Tyr Ser Cys Leu Ala
1               5                   10                  15

Phe Pro Gln Leu Ser Pro Thr Phe Thr Val Thr Ile Pro Gly Gly Arg
            20                  25                  30

Val Cys Ser Asn Ala Lys Tyr Ala Met Ile Cys Asp Lys Gln Ala Met
        35                  40                  45

Arg Val Lys Arg Ala Lys Gly Val Gly Leu Cys Leu Asp Glu Ser Cys
    50                  55                  60

Phe Arg Gly Ile Cys Asn Cys Gln Arg Met Ser Phe Gly Asn Val Arg
65                  70                  75                  80

Val

<210> SEQ ID NO 15
<211> LENGTH: 81
<212> TYPE: PRT
<213> ORGANISM: Equine arteritis virus

<400> SEQUENCE: 15

Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Ala Ile Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Ile Cys Asn Cys Gln Arg Met Ser Phe Gly Asn Val Arg
65                  70                  75                  80

Val

<210> SEQ ID NO 16
<211> LENGTH: 81
<212> TYPE: PRT
<213> ORGANISM: Equine arteritis virus

<400> SEQUENCE: 16

Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Leu Ile Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Ile Cys Asn Cys Gln Arg Met Ser Phe Gly Asn Val Arg
65                  70                  75                  80

Val
```

<210> SEQ ID NO 17
<211> LENGTH: 81
<212> TYPE: PRT
<213> ORGANISM: Equine arteritis virus

<400> SEQUENCE: 17

Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Val Ile Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Ile Cys Asn Cys Gln Arg Met Ser Phe Gly Asn Val Arg
65                  70                  75                  80

Val

<210> SEQ ID NO 18
<211> LENGTH: 81
<212> TYPE: PRT
<213> ORGANISM: Equine arteritis virus

<400> SEQUENCE: 18

Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Thr Ile Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Ala Cys Asn Cys Gln Arg Met Ser Phe Gly Asn Val Arg
65                  70                  75                  80

Val

<210> SEQ ID NO 19
<211> LENGTH: 81
<212> TYPE: PRT
<213> ORGANISM: Equine arteritis virus

<400> SEQUENCE: 19

Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Thr Ile Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Arg Cys Asn Cys Gln Arg Met Ser Phe Gly Asn Val Arg
65                  70                  75                  80

Val

<210> SEQ ID NO 20
<211> LENGTH: 81
<212> TYPE: PRT

<213> ORGANISM: Equine arteritis virus

<400> SEQUENCE: 20

Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Thr Ile Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Ser Cys Asn Cys Gln Arg Met Ser Phe Gly Asn Val Arg
65                  70                  75                  80

Val

<210> SEQ ID NO 21
<211> LENGTH: 81
<212> TYPE: PRT
<213> ORGANISM: Equine arteritis virus

<400> SEQUENCE: 21

Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Thr Ile Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Trp Cys Asn Cys Gln Arg Met Ser Phe Gly Asn Val Arg
65                  70                  75                  80

Val

<210> SEQ ID NO 22
<211> LENGTH: 81
<212> TYPE: PRT
<213> ORGANISM: Equine arteritis virus

<400> SEQUENCE: 22

Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Ala Val Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Ile Cys Asn Cys Gln Arg Met Ser Phe Gly Asn Val Arg
65                  70                  75                  80

Val

<210> SEQ ID NO 23
<211> LENGTH: 81
<212> TYPE: PRT
<213> ORGANISM: Equine arteritis virus

<400> SEQUENCE: 23

```
Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Ala Val Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Ala Cys Asn Cys Gln Arg Met Ser Phe Gly Asn Val Arg
65                  70                  75                  80

Val
```

<210> SEQ ID NO 24
<211> LENGTH: 81
<212> TYPE: PRT
<213> ORGANISM: Equine arteritis virus

<400> SEQUENCE: 24

```
Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Ala Val Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Arg Cys Asn Cys Gln Arg Met Ser Phe Gly Asn Val Arg
65                  70                  75                  80

Val
```

<210> SEQ ID NO 25
<211> LENGTH: 81
<212> TYPE: PRT
<213> ORGANISM: Equine arteritis virus

<400> SEQUENCE: 25

```
Gly Tyr Asn Pro Pro Gly Asp Gly Ala Cys Gly Tyr Ser Cys Leu Ala
1               5                   10                  15

Phe Pro Gln Leu Ser Pro Thr Phe Thr Val Ala Val Pro Gly Gly Arg
            20                  25                  30

Val Cys Ser Asn Ala Lys Tyr Ala Met Ile Cys Asp Lys Gln His Met
        35                  40                  45

Arg Val Lys Arg Ala Lys Gly Val Gly Leu Cys Leu Asp Glu Ser Cys
    50                  55                  60

Phe Arg Gly Trp Cys Asn Cys Gln Arg Met Ser Phe Gly Asn Val Arg
65                  70                  75                  80

Val
```

<210> SEQ ID NO 26
<211> LENGTH: 5
<212> TYPE: PRT
<213> ORGANISM: Equine arteritis virus

<400> SEQUENCE: 26

```
Arg Leu Ile Gly Gly
1               5
```

-continued

```
<210> SEQ ID NO 27
<211> LENGTH: 5
<212> TYPE: PRT
<213> ORGANISM: Equine arteritis virus

<400> SEQUENCE: 27

Arg Leu Arg Gly Gly
1               5
```

LIVE ATTENUATED REPLICATION-COMPETENT ARTERIVIRUSES HAVING DECREASED DUB/DEISGYLATING ACTIVITY

The present invention relates to replication-competent Arteriviruses, to their use as a medicament, their use as a vaccine and in prophylaxis, to vaccines comprising such Arteriviruses and to Arteriviral PLP2-ubiquitin complexes.

The Arterivirus family belongs to the order Nidovirales, of which currently four species are known: Equine arteritis virus (EAV), Porcine respiratory and reproductive syndrome virus (PRRSV), Lactate dehydrogenase elevating virus (LDV), and Simian hemorrhagic fever virus (SHFV). LDV and SHFV have only minor economic impact, since they infect mice and monkeys respectively. Contrary to this, EAV and especially PRRSV pose a considerable financial burden on society.

Equine arteritis virus causes infections in horses, and thus forms a recurring problem in the horse breeding industry. Therefore it poses a significant economic burden on horse breeders. The Equine arteritis virus establishes a persistent infection in so-called "carrier stallions", which subsequently transmit the virus to mares, potentially leading to abortion of foetuses.

Horse breeders carefully monitor the presence of EAV, especially in stallions, and a number of vaccines have been developed against the virus based on live attenuated virus or based on expression of EAV structural subunits. However, recent outbreaks in New Mexico, US (2006) and France (2007) have increased interest in EAV among veterinarians and horse owners. And although diagnostic tools and vaccines are available, currently available vaccines should be improved (vide infra).

PRRSV is by far the most economically important arterivirus, affecting swine farming industries around the world. Infection with this virus results in slow growth, decreased feed efficiency, anorexia, and fever in weaning to finishing pigs, abortion in pregnant sows and respiratory problems in young pigs. In the US alone, yearly losses associated with PRRSV infection were estimated to lie around $ 560 million in 2005 and $ 664 million in 2011. PRRSV infection ranks as the number one health challenge for the pig industry, causing the greatest productivity losses when compared to other diseases caused by for example *Clostridium difficile*, swine influenza, *Streptococcus* sp., rotavirus or porcine circovirus. Considering the emergence of highly virulent strains of PRRSV in South-East Asia in 2006 and the fact that the Asian swine industry is the largest in the world, it can safely be assumed that losses in this part of the world are considerably higher than those reported for the US.

PRRSV remains a major threat to the swine industry since the associated disease has proven to be difficult to control, in spite of the availability of both live attenuated and killed vaccines against PRRSV.

Live attenuated vaccines usually comprise a virus that is produced by serial passage of strains in cell culture, resulting in attenuated viruses that do no longer induce disease in pigs. These vaccines generally induce some level of long-lasting protection. However when derived from a single PRRSV vaccine strain they may not fully protect against heterologous PRRSV infection (PRRSV isolates can be highly diverged and group into a European and a North-American genotype). Additionally, vaccination with live attenuated vaccines may not completely prevent reinfection with wild-type virus, and transmission of vaccine virus through vaccinated herds was observed on several occasions. Also, reversion to virulence of vaccine strains has been observed. (Storgaard, T. et al., (1999), Botner, A. et al., (1997), Nielsen, H. S. et al., (2001)).

Moreover, since currently no commercially available marker vaccines exist, it is impossible to discriminate between vaccinated and naturally infected animals.

Killed virus vaccines are also available and they are intrinsically much safer, since they do not involve replicating virus. However, on the down-side, the lack of viral replication is probably the main reason why these vaccines are generally less effective.

An additional complicating factor in the development of efficacious arterivirus vaccines in general lies in the fact that Arteriviruses are believed to evade the host's innate immune responses. In general, it is believed that the strong immunomodulatory capabilities of Arteriviruses prevent the induction of an efficient immune response by (live attenuated) vaccines. Therefore the level of immunity that can be induced may be suboptimal for protecting against challenging viruses.

Thus there is a need for alternative approaches to diminish or even solve the problems associated with the classical killed and live attenuated arterivirus-based vaccines.

The Arterivirus family consists of positive-sense (+) single-stranded RNA viruses with a genome size ranging from about 13 to 16 kb. Upon infection, the RNA is translated into two replicase precursor polyproteins, pp1a and pp1ab. The functional non-structural proteins (nsps) of Arteriviruses derive from cleavage of these polyproteins by internally encoded proteases. Upon release from the polyprotein, these non-structural proteins together form the replication and transcription complex which is responsible for the replication of the viral genome and for the synthesis of the subgenomic messenger RNAs encoding the structural proteins. The pp1a and pp1ab polyproteins of the prototype Arterivirus, EAV, are cleaved into at least 13 nonstructural proteins by three internal proteases present in nonstructural protein 1 (nsp1), nsp2 and nsp4. Arteriviral nsp2 contains a papain-like protease (PLP) domain in its N-terminal region. PLP2, as this protease is commonly referred to, is responsible for the cleavage of the junction between nsp2 and nsp3, and its catalytic activity is, likely for this reason, essential for viral replication. (Older literature often refers to this protease as CP (cysteine protease) or nsp2 CP).

In addition to its role in polyprotein processing, nsp2 was more recently found to also play a role in the evasion of host innate immune responses, as indicated above. Upon infection, the presence of viral nucleic acids can trigger the activation of innate immune signaling cascades, resulting in the activation of transcription factors such as NFκB and Irf3/Irf7, ultimately leading to the transcription of genes encoding beta interferon (IFN-β) and other pro-inflammatory cytokines. Besides through protein phosphorylation, these signaling pathways are extensively regulated, both positively and negatively, through protein ubiquitination (Jiang, X. (2012)). Interest in a possible immune evasive activity of nsp2 was raised when comparative sequence analysis showed that the PLP2 domain of this protein displayed a very remote similarity to proteins belonging to the ovarian tumor domain-containing (OTU) class of de-ubiquitinating enzymes (DUBs) (Makarova (2000)). It has since then been confirmed that Arteriviral PLP2 indeed possess genuine DUB activity and that this activity is likely employed to remove ubiquitin (further also referred to as Ub) from innate immune signaling factors to suppress or reduce the induction of an antiviral state (Frias-Staheli, N. (2007), Sun, Z. (2010), van Kasteren, P. B. (2012)). In addition to its DUB activity, arteriviral PLP2 has also been shown to remove the ubiquitin-like antiviral protein Interferon Stimulated Gene 15 (ISG15) from cellular target proteins (Frias-Staheli, N. (2007), Sun, Z. (2012), Arguello, M. D. (2007)). This activity will be referred to as the deISGylating activity. Due to the close relatedness of ubiquitin and ISG15, this role of the PLP2 domain will generally be referred to as the DUB/deISGylating activity.

There is clearly a very close link between the polyprotein processing function and the DUB/deISGylating activity, since both activities rely on the same catalytic core amino acid residues in PLP2. Furthermore, the sequence defining the nsp2/nsp3 cleavage site within Arterivirus replicase polyproteins (xxGG) displays similarity to the canonical C-terminal motif (LRGG) that is found in ubiquitin and ubiquitin-like molecule ISG15, with cleavage occurring immediately after the second glycine residue. As a consequence, this close link makes it very difficult if not impossible to study these substrate specificities independently.

Several preliminary attempts have been described to make modifications in, or close to, the PLP2 domain that would specifically reduce or remove the DUB/deISGylating activity while at the same time keeping the polyprotein processing function at the nsp2/nsp3 junction (without which the virus cannot survive) intact.

Sun et al. (2010) described an attempt to make mutations at several amino acid positions at the N-terminal border of the PLP2 domain of PRRSV. They selected a certain part of the PLP2 domain for introducing mutations, based upon the presence of a B-cell epitope (ES2) in this region. As was to be expected, given the importance of this region in the polyprotein processing activity at the nsp2/nsp3 junction, by far most of the generated PLP2 mutations were lethal to the virus. Only three mutations, at positions D458A, S462A and D465A (numbers refer to Sun et al., 2010) were "tolerated" without causing a complete loss of virus viability. These mutants however showed hardly any or no decrease at all in the inhibition of NFκB activation.

It could only be concluded that mutations made at these positions are either lethal to the virus or lead to viable virus that hardly differs from the wild-type virus in its ability to inhibit NFκB activation through de-ubiquitination. This study demonstrates that it is difficult to separate the intimately linked PLP2 functions in polyprotein processing and DUB/deISGylation.

Sun et al. later selected (Sun 2012) another region for the introduction of mutations in a new attempt to study the possibilities to block the DUB/deISGylating activity while retaining the PLP2 polyprotein processing function. In Sun (2012), a new set of deletions at the N-terminal border of the PLP2 domain of PRRSV is described. Only a deletion spanning the region from amino acid 402-420 of the ORF1a-encoded protein was found to yield a virus that showed a partial decrease in ISG15 antagonist function and was still able to replicate albeit to a very low titer, provided that an additional downstream point mutation was present at position 462. Thus, this virus is for the reasons mentioned not suitable as a basis for a live vaccine virus.

Patent Application WO2012/063212 describes attempts to make modifications that might possibly lead to impaired immune evasion capacities in PRRSV. In this patent application, a mutant virus is described that comprises 32 amino acid changes at locations scattered over the whole viral genome, all outside the PLP2 domain, all of which believed to be directly responsible for the interferon induction/inhibition phenotype of the virus. Thus, all of these changes must be introduced in order to turn a wild-type virus into a replication-competent virus that has a decreased interferon inhibition activity. Since there is no indication at all which amino acid change(s) is/are actually responsible for this inhibitory effect, no prediction about the safety of the virus can be made: it may well be that a single point mutation leads to reversion to virulence which would make this virus a poor vaccine candidate. Moreover, the lack of knowledge about which amino acids are responsible for the attenuated phenotype makes it difficult to construct new vaccine candidates from other strains: apart from the arduous task to introduce 32 amino acid changes in a virus, it is unlikely that these 32 amino acid mutations in the different sequence context of another virus will have the same effect on virus attenuation and reduction of the IFN inhibition.

Patent Application WO2009/008924 describes methods of preventing viral infection by inhibiting the deISGylating activity of OTU-containing viral proteins. The application mainly aims at targeting the deISGylating activity of OTU-containing viral proteins by means of pharmaceutical compounds. However, this application does not disclose or even hint towards modifications in Arteriviruses that specifically remove the DUB/deISGylating activity while at the same time keeping the polyprotein processing function intact.

So basically the known mutations causing a significant decrease in DUB/deISGylating activity inevitably seem to lead to an unacceptable decrease in virus replication or in most cases to no virus replication at all.

The lack of acceptable results so far strongly suggests that it may not be possible at all to disentangle the intimate link between the polyprotein processing function and DUB/deISGylating activity of PLP2.

It is an objective of the present invention to provide viruses of the Arterivirus family that on the one hand are still replication-competent and on the other hand nevertheless display a decreased DUB/deISGylating activity of PLP2.

It was surprisingly found now, that although the PLP2 active site for polyprotein processing function and DUB/deISGylating activity is the same, the substrate binding is different for Ub and ISG15 on the one hand and the nsp2/nsp3 cleavage site on the other hand.

This identification of, on the one hand, the part of the PLP2 domain that binds the beta-grasp fold of Ub or C-terminal beta-grasp fold of ISG15 and, on the other hand, the region involved in binding to an unstructured region of the polyprotein that contains an xxGG motif that is similar to the unstructured region of the C-terminal tail of Ub or ISG15 could now for the first time be done through elucidation and analysis of the 3D-structure of the PLP2 domain of nsp2, more specifically when bound to ubiquitin.

Up to now, it was not possible to determine the 3D-structure of the PLP2 domain, i.a. due to difficulties in growing protein crystals suitable for X-ray crystallography.

A first problem to be solved is related to the production of a sufficient amount of an nsp2-fragment that allowed for crystallographic analysis of the PLP2 domain. Nsp2 expresses poorly in expression systems and, when expressed as a fusion protein, is difficult to remove from the fusion partner without PLP2 becoming insoluble and thus unsuitable for protein crystallization.

It was surprisingly found now that expression of the EAV PLP2 domain (in this case, but not necessarily, residues 261-392 of the polyprotein), in frame with an N-terminal ubiquitin from the expression plasmid pASK3 (Gohara D, et al., (1999)) sufficed to obtain protein that 1) has a native N-terminus, as would have been the case when the protein would originate from a viral polyprotein and 2) could be produced in sufficient quantities for crystallization purposes.

Usually, plasmid pASK3 is used for the expression of proteins in an *E. coli* cell that also expresses the DUB ubiquitin protease 1 (Ubp1), as a result of which the N-terminal ubiquitin tag is cleaved off soon after expression. In the present situation, however, it sufficed to express polyprotein residues 261-392 (i.e. the PLP2 domain of EAV nsp2) in frame with an N-terminal ubiquitin tag using plasmid pASK3 without at the same time expressing DUB Ubp1, due to the fact that PLP2 itself acts as a DUB. Moreover, due to the fact that PLP2 cleaves just behind its recognition site LxGG, a PLP2 fragment was produced with its native N-terminus, as would have been the case when the protein originates from a viral replicase polyprotein cleavage. This special combination of the PLP2 domain of EAV nsp2 and the use of expression plasmid pASK3 provided a protein fragment that indeed has a native N-terminus and is produced in sufficient quantity to allow for a determination of the three-dimensional structure of the PLP2 domain by protein X-ray crystallography.

A second problem encountered in the process of determining the 3D-structure of the PLP2 domain was the inability to crystallize the purified PLP2 domain. In order to overcome this problem, in a next step, the mechanism-based suicide inhibitor $Ub_{(1-75)}$-3-bromopropylamine (Ub-3Br) was prepared according to Messick et al (2008) and Borodovsky et al (2002) as described by James et al (2011). Then, Ub-Br3 was covalently bound to purified PLP2 by gently mixing the proteins in a 3:2 molar ratio, respectively, for one hour at 37° C. The resulting PLP2-ubiquitin complex was purified by gel filtration, anion exchange (Source 15Q) chromatography and then exchanged into 20 mM Tris, pH 8.0, 50 mM NaCl before concentrating to 10 mg/ml and storing at 4° C.

The formation of this PLP2-ubiquitin complex which was stabilized by a covalent bond between the catalytic nucleophile of the PLP2 domain (Cys 270) and the C-terminus of ubiquitin, yielded a complex that was stable enough to crystallize and allow the 3D-structure of the complex to be determined by X-ray crystallography. The PLP2-Ub complex was crystallized by hanging-drop vapor diffusion.

The Examples section provides further detailed information regarding the crystallization process.

As stated above, the crystal structure of the EAV PLP2 domain (residues 261-392 of EAV pp1a; 13.6 kDa) was determined as a covalent complex with the mechanism-based inhibitor Ub-Br3. Since conservation of multiple cysteine residues and their demonstrated importance for protease functionality suggested that PLP2 could bind zinc (Snijder et al., 1995), the crystal structure of the complex was determined by a multi-wavelength anomalous dispersion (MAD) phasing experiment using X-ray diffraction data collected over the zinc absorption edge. The resulting electron density map revealed residues 261-387 of PLP2 bound to a complete ubiquitin molecule and allowed a model of the complex to be built and refined ($R_{work}$=0.16, $R_{free}$=0.18) to 1.45 Å resolution (FIG. 1A).

PLP2 adopts a compact, two-domain fold with a shallow Ub-binding site that directs the C-terminus of the bound Ub molecule (the 'distal' Ub in a Ub dimer) towards a solvent exposed active site (FIG. 1A). Domain I of PLP2 (residues 267-307 and 365-378) consists of a three-helix bundle ($\alpha1$, $\alpha2$, $\alpha4$) packed against a two-stranded antiparallel sheet ($\beta2\uparrow$ $\beta6\downarrow$). Domain II centers on a four-stranded $\beta$-sheet ($\beta1\uparrow$ $\beta5\downarrow$ $\beta4\uparrow$ $\beta3\uparrow$) and an $\alpha$-helix ($\alpha3$) that together pack against helices $\alpha1$ and $\alpha2$ of domain I. Domain II comprises the majority of the Ub-binding site, which is stabilized by four cysteine residues (Cys 319, 349, 354, 356) that coordinate a zinc ion with tetrahedral geometry (FIG. 1B). Their arrangement forms a C4 zinc finger that resembles a C-terminal type zinc necklace motif (Andreini et al., 2011) (FIG. 1B). A large insertion between positions C1 (Cys319) and C2 (Cys349) appears to extend the stabilizing effect of the zinc finger throughout much of domain II. A fifth cysteine (Cys344) is located near the zinc ion but does not coordinate with it, consistent with other zinc necklace motifs that have been described (Andreini et al., 2011) and with previous findings showing that a Cys344 to alanine mutation had no effect on catalytic activity of the PLP2 domain (Snijder et al., 1995). Three of the cysteines (Cys 319, 349, and 354) are fully conserved in Arteriviruses, and mutational analysis of these residues and Cys356 demonstrated their presence to be essential for catalytic activity (Snijder et al., 1995). Given its distance from the active site however (~25 Å) (FIG. 1A), the zinc finger appears to play a structural role as opposed to participating in catalysis. Expression of the PLP2 domain in *E. coli* grown in the absence of zinc (M9 media) yields insoluble protein, supporting the idea that the zinc finger is structural and is likely required for correct folding of the protease.

The PLP2 active site contains a catalytic cysteine nucleophile (Cys270) and histidine (His332) residue, along with an accompanying asparagine (Asn263) that hydrogen bonds with the imidazole ring of His332 (FIG. 1C). The side chain of Cys270 is covalently coupled to the C-terminus of Ub via the 3-propylamine (3CN) modification, mimicking the acylenzyme intermediate step of the catalytic reaction and confirming the identity of Cys270 as the catalytic nucleophile (FIG. 1A, C).

The Arterivirus PLP2 deviates from typical OTU-domain structures. Members of the OTU superfamily classify as structural relatives of Arterivirus PLP2, supporting its classification as a member of this superfamily. However, the sequence similarity between Arterivirus PLP2 and OTU-domain proteases is very weak (Makarova et al., 2000) and indeed the EAV PLP2 structure exhibits topological features that deviate considerably from a typical OTU-fold. Domain I of known OTU-domain structures contains a pair of solvent exposed alpha helices that pack perpendicularly against two internal helices (FIG. 1D, G, H). While the internal helices are conserved in PLP2 ($\alpha1$ and $\alpha2$), the solvent exposed helices are replaced by a single helix ($\alpha4$) that packs parallel to helices $\alpha1$ and $\alpha2$ to form the three-helix bundle described above (FIG. 1A, F). This topology subtly resembles the L domain of papain (Kamphuis et al., 1984) and markedly reduces the size of domain I of PLP2 and its contribution to Ub binding relative to other OTU-domain DUBs that have been determined in complex with Ub (Akutsu et al., 2011; Capodagli et al., 2011; Huang et al., 2012; James et al., 2011; Messick et al., 2008).

A more striking deviation from known OTU-domain structures is the presence of the zinc finger in domain II of PLP2 (FIG. 1A, B) and its critical importance for catalytic activity (Snijder et al., 1995). Ub-binding domains containing zinc fingers exist within a number of OTU-domain DUBs, but none comprise part of the distal Ub binding site within the OTU-domain fold. They exist instead as accessory domains that are connected to the OTU-domain through flexible linkers (Komander et al., 2009), where, in the case of A20, they appear to provide additional polyubiquitin linkage specificity and possibly target the protein to specific signaling complexes (Bosanac et al., 2010). For PLP2, the zinc finger motif is an integral part of the OTU-fold and, as described below, plays a central role in binding and positioning the distal Ub molecule on the protease surface (FIG.

1). Currently, OTU-domain DUBs are grouped into three subclasses based on their structural characteristics: the Otubains, the A20-like OTU's and the OTU's (Komander et al., 2009).

Given the surprising unique features of EAV PLP2, the inventors now believe that Arterivirus PLP2 enzymes represent a new (a fourth) subclass of zinc-dependent OTU's. Arterivirus PLP2 and CCHFV OTU are unique from eukaryotic OTU-domain DUBs in that they remove ISG15 from cellular targets in addition to Ub.

The crossreactivity towards ISG15-tagged substrates observed for CCHFV OTU arises primarily from a unique β-hairpin on the Ub-binding site that modifies the site such that it can accommodate both Ub and the C-terminal Ub-like domain of ISG15 (Akutsu et al., 2011; James et al., 2011).

It was surprisingly found now that, although Arterivirus PLP2 also exhibits crossreactivity towards ISG-tagged substrates, the β-hairpin structure is completely absent in PLP2 and replaced by helix α3 of the zinc-finger motif. Interestingly, in keeping with the role of the β-hairpin on CCHFV OTU, residues of helix α3 bind to the hydrophobic 'Ile44 patch' of Ub, a site commonly targeted by Ub binding proteins (Dikic et al., 2009), and assist in binding of Ub to the PLP2 domain in a manner equivalent to that observed for CCHFV OTU (FIG. 1E). This binding mode allows CCHFV OTU to accommodate additional bulky residues on ISG15 that are not present on Ub, a feature that appears to be present in the EAV PLP2 domain as well.

As said above, in addition to its isopeptidase activity targeting Ub and ISG15, Arterivirus PLP2 also cleaves a specific peptide bond within the viral polyproteins as part of the replicase polyproteins' maturation process. Given the distance of helix α3 from the PLP2 active site (FIG. 1A), it could now, for the first time, be determined that mutations could be introduced into this region of the Ub-binding site that would selectively disrupt PLP2's DUB and deISGylating activities without affecting the ability of the enzyme to bind and cleave the linear nsp2/nsp3 junction within the viral polypeptide. This finding was strengthened by the observation that although the putative nsp2/nsp3 cleavage site (828-RLIGG↓-832; SEQ ID NO: 26) of EAV closely resembles the C-terminal tail of Ub and ISG15 (RLRGG↓; SEQ ID NO: 27), the nsp2 sequence upstream of the cleavage site does not appear to have a Ub-like fold, indicating that the majority of the PLP2 Ub-binding site is not required for the enzyme to recognize and cleave the nsp2/nsp3 junction.

It is one of the merits of the present invention that the 3D-structure for the PLP2 domain of Ariviruses is now elucidated, and what's more: at 1.45 Å resolution. Thus, it is now for the first time possible to perform a structure-guided decoupling of PLP2 deubiquitinase and polyprotein cleavage activities; it can now for the first time rationally be decided which regions of the PLP2 domain in any Arterivirus can or can't be modified in order to provide Ariviruses according to the present invention, i.e. Ariviruses that are still replication-competent but have a decreased DUB/deISGylating activity.

Figure 2:
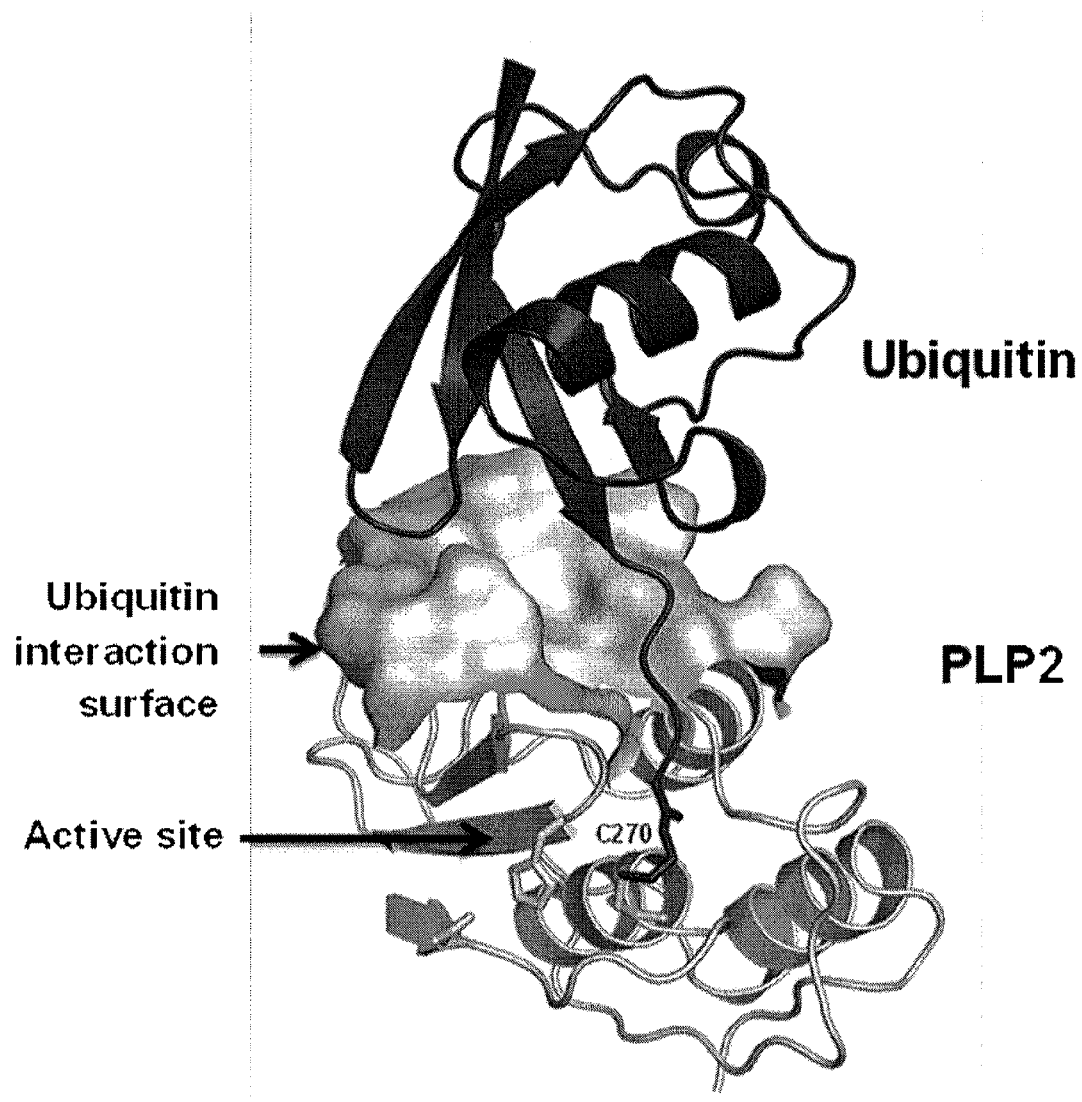

Merely as an example, the 3D-structure of PLP2, ubiquitin and the PLP2-ubiquitin binding surface is given in FIG. 2 for the Arterivirus EAV, more specifically for strain Bucyrus (GeneBank accession number NC_0022532).

However, the following is emphasized here; the newly developed combination of expression methods and crystallization methods provided here in order to obtain the crystal structure of a PLP2-ubiquitin complex is generally applicable to the PLP2 domain of any Arterivirus.

It is also important to realize in this respect, that it is primarily the 3D-structure of the PLP2 domain that determines the ubiquitin binding surface, not so much the mere amino acid sequence of that domain. This follows immediately from the multiple sequence alignment given in FIG. 3. This structurally functional alignment includes the PLP2 sequences of the EAV Bucyrus strain as well as three representative but distinct PRRSV strains: GM2 (a Chinese field strain), Lelystad (a prototypical European strain) and VR-2332 (a prototypical North American strain). It can be seen at once, that there is a significant number of differences between the various Arterivirus sequences, both with regard to the characteristics of individual amino acids and with regard to the difference in the number of amino acids in the various strains, resulting in gaps that are present at several locations in the alignment. Nevertheless, the 3 D-structures of the ubiquitin binding surface of the PLP2 domain of EAV Bucyrus strain and those predicted by comparative molecular modeling for the PRRSV strains GM2, Lelystad and VR-2332 are strikingly similar. This is illustrated in FIG. 4, where the structural models of PLP2-ubiquitin of EAV strain Bucyrus, PRRSV strain Lelystad and PRRSV strain VR-2332 are shown. Again, it can immediately be seen that, in spite of the differences in amino acid sequence and numbers, the ubiquitin binding surface of the PLP2 domain of EAV and the two PRRSV strains are strikingly similar.

And in fact this is in line with the expectations: all Arteriviral PLP2 domains employ the same catalytic core and due to the very complex substrate specificity of this protease, the 3D-structure must be well-conserved among the various members of the Arterivirus family.

Thus, a first embodiment of the present invention relates to replication-competent Arterivirus, characterized in that said virus has a decreased DUB/deISGylating activity due to a mutation in the PLP2 domain of the non-structural protein nsp2.

The PLP2 domain of the non-structural protein nsp2 is a very short domain: the PLP2 domain of e.g. EAV strain Bucyrus consists of only 127 amino acids (SEQ ID NO.: 9) and that of PRRSV strain Lelystad consists of only 136 amino acids (SEQ ID NO.: 10).

The PLP2 domain of e.g. PRRSV strain VR-2332 consists of 139 amino acids (SEQ ID NO.: 11) FIG. 3 represents a sequence alignment of the PLP2 domain for EAV strain Bucyrus, PRRSV strain Lelystad, PRRSV strain VR-2332 and PRRSV strain GM2 (vide infra). FIG. 4 shows the molecular models of VR-2332 and Lelystad based on the alignment of their respective sequences to EAV PLP2. Once aligned to EAV PLP2, this allows the sequences of either VR-2332 or LV to be substituted onto the 3D backbone structure of the EAV PLP2 crystal structure. In other words, the amino acid side chains of the EAV PLP2 domain are replaced by those of VR-2332 or LV as dictated by the multiple sequence alignment. From there, missing loops are modelled ab initio and the overall 3D model is optimized using an appropriate energy minimising target function.

The numbering of the amino acid sequence of the PLP2 domain of EAV as given in FIG. 3 is used in order to refer to the various boxed regions. This numbering is therefore referred to as "consensus numbering" of the PLP2 domain.

As defined herein, a replication-competent Arterivirus is a virus that can still replicate, i.e. is capable of producing infectious progeny virus. The infectious progeny virus can be replication-competent infectious progeny virus or replication-defective infectious progeny virus. Replication-competent viruses according to the invention are very suitable as a basis for live attenuated Arterivirus vaccines. However, in order to produce sufficient amounts of virus for use in a vaccine, the amount of progeny virus must be sufficiently high. Therefore, for the purpose of this invention, a replication-competent virus is a virus that produces an amount of progeny virus in a susceptible cell system, that it not more than $3^{10}$ logs below the amount of progeny virus produced by the same virus without a mutation according to the invention in the same cell system. Merely as an example: if a certain amount of a PRRSV strain produces 1,000,000 infectious progeny virus particles in a certain cell culture system, the same strain carrying a mutation according to the invention must produce 1000 infectious particles or more to qualify as replication-competent virus.

Preferably, the amount of progeny virus is not more than $2^{10}$ logs below the amount of progeny virus that a virus without a mutation according to the invention would produce in the same cell system.

More preferably, the amount of progeny virus is not more than $1^{10}$ log below that amount.

For the purpose of this invention, an Arterivirus according to the invention having a decreased DUB/deISGylating activity is a virus that has a mutation in the PLP2 domain such that said virus shows an increase in interferon beta mRNA induction to a level that is at least twice the amount of interferon beta mRNA induction shown by a wild-type virus.

In the Examples section, a description is given of a real time quantitative PCR reaction that can be used to determine the level of interferon beta mRNA induction. In that Example, the level of interferon beta mRNA induction of EAV wild type virus and mutants according to the invention is tested and compared.

The necessary primers for EAV IFN beta mRNA testing in RT-PCR are provided in table 2. In Artursson K, et al., J. Interferon Res. 12(3):153-160 (1992), the sequence of a porcine IFN beta is provided, allowing the skilled person to design comparable primers for a real time PCR reaction that can be used to determine the level of IFN beta mRNA induction of PRRS virus mutants according to the invention.

In FIG. 9A, it is shown that e.g. EAV mutant I353R produces about 4 times as much IFN beta mRNA compared to the wild type virus that does not comprise the I353R mutation. The triple-mutant in FIG. 9A even produces about 8 times as much IFN beta mRNA compared to the wild type virus.

As can be seen from FIG. 6B, a mutant such as T312A already shows a level of DUB-activity that leads to a significantly denser alpha-flag lane, which represents the amount of remaining ubiquitin conjugates, than that of the wild-type virus. The adjacent I353R lane, for which the corresponding mutated virus shown in FIG. 9A produced four times as much IFN beta compared to the wild-type virus, shows a density of the alpha-flag lane that is about twice as high as that of the T312A lane.

For this reason, the inventors consider a virus that has a mutation in the PLP2 domain such that said virus shows an increase in interferon beta mRNA induction to a level of at least twice, preferably four, more preferably eight times the amount of interferon beta mRNA induction shown by a wild-type virus, to be a virus having a decreased DUB/deISGylating activity.

For the purpose of this invention, a mutation can e.g. be a replacement, an insertion or a deletion, as explained below.

In FIG. 3 an overview is given of the PLP2 domain of four different examples of Arteriviruses: EAV strain Bucyrus, and PRRSV strains GM2, Lelystad and VR-2332. An alignment of the sequences is made and relevant regions are indicated by boxes. This figure should be seen in close connection with FIGS. 2 and 4. FIG. 2 shows the 3D-structure of the PLP2 domain of EAV and the way ubiquitin binds to this structure. FIG. 4 shows the predicted 3 D-structure of the PLP2 domain of PRRSV strains Lelystad and VR-2332 and the way ubiquitin binds to this structure, side-by-side with the crystal structure of the PLP2 domain of EAV strain Bucyrus for comparison.

Residues in FIG. 3 that are boxed with dotted lines represent residues that interact near the active site with the RLRGG motif of ubiquitin. Mutating these residues is likely to affect the polyprotein processing activity of the PLP2 domain and should thus preferably be avoided. Residues boxed with thick lines represent residues that bind directly to the beta-grasp fold of ubiquitin (i.e. the main body of ubiquitin), not near the active site.

The zinc-binding site and residues immediately surrounding this site form the majority of the ubiquitin interactions surface of the PLP2 domain that binds the beta-grasp fold of ubiquitin and likely the analogous region of the C-terminal domain of ISG15.

As said above (and as can be seen from the alignment in FIG. 3), it is the 3D-structure that determines which amino acid residues form the ubiquitin interaction surface. This follows also from FIG. 4C, where it is shown that for the PRRSV strain Lelystad, i.a. Thr478, Val479 and Val520 are predicted to bind to ubiquitin, whereas for PRRSV strain VR-2332 this role is played by Ala486, Leu487 and Cys528 and for EAV strain Bucyrus, this role is played by Thr312, Ile313 and Ile353.

In a preferred form of the first embodiment of the present invention, the replication-competent Arterivirus, having a decreased DUB/deISGylating activity due to a mutation in the PLP2 domain of nsp2 is selected from the group of viruses consisting of EAV and PRRSV.

FIG. 3 represents structurally aligned sequences defining the ubiquitin interaction surface alignment of 4 Arterivirus sequences representing major EAV and PRRSV strains. The alignment is indeed structural in the sense that the boxes indicate regions of each of the PLP2 amino acid sequences that in all cases interact with ubiquitin, according to either the crystal structure (EAV) or the models (PRRSV) as shown side-by-side in FIG. 4.

From FIGS. 3 and 4C, it can be seen which amino acids in one Arterivirus correspond to that of another Arterivirus, for example I313 in EAV=V479 in LV, and L487 in VR2332, with respect to their position in the interaction surface with ubiquitin.

In order to obtain a replication-competent Arterivirus, having a decreased DUB/deISGylating activity due to a mutation in the PLP2 domain of the non-structural protein nsp2, one would in view of FIG. 3 preferably make mutations in and/or close to the regions boxed with thick lines in the structurally aligned PLP2 sequences.

The amino acid numbering in FIG. 3 is represented here for four examples of Arteriviruses: for EAV strain Bucyrus and for PRRSVs Lelystad, VR-2332 and GM2. It is clear that other Arterivirus PLP2 sequences can equally be structurally aligned with the sequences already given in FIG. 3. As indicated above, for ease of reference, the numbering of the amino acid sequence of the PLP2 domain of EAV as given in FIG. 3 is used in order to refer to the various boxed regions.

Thus, a more preferred form of this embodiment relates to a replication-competent Arterivirus according to the invention, characterized in that said mutation in the PLP2 domain is located at any of consensus positions 296-297 and/or 309-319 and/or 326-330 and/or 345-355 according to the EAV numbering as depicted in FIG. 3. In this figure, the positions for PRRSV Lelystad are 463-464, 475-485, 492-496 and 512-522 respectively. For PRRSV VR-2332 and PRRSV GM2, the positions are 471-472, 483-493, 500-504 and 520-530.

An even more preferred form of this embodiment relates to a replication-competent Arterivirus according to the invention, characterized in that said mutation in the PLP2 domain is located at any of consensus positions 296-297 and/or 310-318 and/or 327-329 and/or 346-354 according to the EAV numbering as depicted in FIG. 3.

Merely as an example; these positions for e.g. PRRSV Lelystad are 463-464, 476-484, 493-495 and 513-521.

A still even more preferred form of this embodiment relates to a replication-competent Arterivirus according to the invention, characterized in that said mutation in the PLP2 domain is located at any of consensus positions 296-297 and/or 311-317 and/or 328 and/or 347-348 and/or 351-353 according to the EAV numbering as depicted in FIG. 3.

The inventors demonstrated, as an example, through site directed mutagenesis that e.g. positions Thr312, Ile313 and Ile353 of the EAV PLP2 ubiquitin interaction surface to be important for the DUB activity of the enzyme and the ability of the EAV virus to suppress the IFN response. The analogous positions in PRRSV strains Lelystad (Thr478, Val479 and Val520) and VR2332 (Ala486, Leu487 and Cys528) and neighboring amino acids within the regions identified as important for DUB and deISGylating activity can also mutated to achieve the same effect in PRRSV. Given that positions Ile313 (Val479 of Lelystad PLP2, Leu487 of VR2332 PLP2) and Ile353 (Val520 of Lelystad PLP2, Cys528 of VR2332 PLP2) of the EAV PLP2 domain are on the solvent-exposed surface of the ubiquitin interaction surface, these positions on Lelystad or VR2332 PLP2 domains could be mutated to a variety of amino acids to selectively disrupt DUB and deISGylating activity. Such amino acids e.g. include Ala, Arg, Ser, Thr, Trp (for which the inventors already demonstrated that it can be tolerated at position 353 in the EAV PLP2 domain).

The side chain of Thr312 of EAV PLP2 (Thr478 of Lelystad PLP2, Ala486 of VR2332 PLP2) is packed within a tight loop, thus mutations at this position need to more conservative as they could misfold the loop. Possible mutations at this position include e.g. Gly (for EAV, Lelystad and VR2332), Ala or Ser (EAV and Lelystad).

A most preferred form of this embodiment relates to a replication-competent Arterivirus according to the invention, characterized in that said mutation in the PLP2 domain is at consensus position T312, I313 or I353.

A specific form of this most preferred form relates to a replication-competent Arterivirus according to the invention, characterized in that said Arterivirus is EAV and said mutation in the PLP2 domain is T312A, I313V, I353A, I353R, I353S, I353T or I353W In addition to residues of the ubiquitin interaction surface of the PLP2 domain that bind directly to ubiquitin (boxed by thick lines in FIG. 3), there exist a number of residues that structurally support the ubiquitin interaction surface and assist in defining the shape of this surface such that it is complementary to the structure of ubiquitin (and ISG15). Based on the 3D crystal structure of the EAV PLP2 domain and comparative molecular models of the PLP2 domain from PRRSV strains Lelystad and VR-2332, residues 303-306 of EAV PLP2 (470-473 of Lelystad PLP2 and 478-481 of VR-2332 PLP2) play an important role in placing helix 2 underneath the ubiquitin interaction surface of the PLP2 enzymes. Mutation of residues within this region could be used to affect proper placement of helix 2, leading to distortion of the ubiquitin interaction surface and thus reduced DUB/deISGylating activity. Given these residues are distant from the PLP2 active site, their mutation could be used to reduce DUB/deISGylating activity with minimal effect on viral polyprotein processing.

Thus, another more preferred form of this embodiment relates to a replication-competent Arterivirus according to the invention, characterized in that said mutation in the PLP2 domain is located at any of consensus positions 303-306 according to the EAV numbering as depicted in FIG. 3. In this figure, the positions for PRRSV Lelystad are 470-473. For PRRSV VR-2332, the positions are 478-481.

Similarly, residues 343-346 of EAV PLP2 (510-513 of Lelystad PLP2 and 518-521 of VR-2332 PLP2) assist in positioning helix 3 of the zinc finger motif, a structure that forms a number of key binding interactions with Ub. Mutation of residues within this region could be created to distort the position of the zinc finger motif and surrounding ubiquitin interaction surface to selectively reduce DUB/deISGylating activity without affecting viral polyprotein processing.

Therefore, again another more preferred form of this embodiment relates to a replication-competent Arterivirus according to the invention, characterized in that said mutation in the PLP2 domain is located at any of consensus positions 343-346 according to the EAV numbering as depicted in FIG. 3. In this figure, the positions for PRRSV Lelystad are 510-513. For PRRSV VR-2332, the positions are 518-521.

Moreover, EAV PLP2 residue Phe350 (Val517 of Lelystad PLP2 and Val525 of VR-2332 PLP2) is located on helix 3 of the zinc finger and participates in packing helix 3 against α-helix 2. Given the importance of helix 3 in binding ubiquitin, mutation of EAV PLP2 residue Phe350 (Val517 of Lelystad PLP2 and Val525 of VR-2332 PLP2) could be used to displace the helix 3, thereby selectively reducing DUB/deISGylating activity.

Thus, still another more preferred form of this embodiment relates to a replication-competent Arterivirus according to the invention, characterized in that said mutation in the PLP2 domain is located at consensus position 350 according to the EAV numbering as depicted in FIG. 3. In this figure, the position for PRRSV Lelystad is 517. For PRRSV VR-2332, the position is 525.

The types of residue mutations that can be introduced into the regions of the PLP2 enzymes deemed important for DUB and deISGylating activity depend on the local environment of the residue(s) to be mutated and can be determined by the skilled person without undue burden. For example, if the residue is on the surface of the ubiquitin interaction surface and has a hydrophobic side chain (e.g. Leucine) that packs against a hydrophobic region of ubiquitin, allowable mutations could include: 1) complete removal of the side chain (i.e. substitute with glycine), 2) substitution with a polar side chain to electrostatically disrupt the hydrophobic interaction (e.g. Asp, Glu, Ser etc.), 3) Substitution with a large, bulky residue to sterically disrupt the interaction (e.g. Trp, Arg, Lys). Note; Arg and Lys are both polar and bulky, which would provide a synergistic effect, leading to considerable disruption of the interaction at this position. Combinations of such mutations across the ubiquitin interaction surface could be used to achieve maximal reduction in DUB and deISGylating activity.

If the targeted residue is a buried hydrophobic residue, then substitutions need to be more conservative, this is, the substitution should preferably be another hydrophobic residue to retain overall proper protein folding, but with an altered shape so as to distort the ubiquitin interaction surface to reduce DUB and deISGylating activity.

If the targeted residue forms an important electrostatic interaction needed for protein stability, then only those substitutions that retain this interaction can be introduced at this location.

Examples of the above mutagenesis guidelines can be observed for substitutions that have been made in the EAV PLP2 enzymes (table 1). For example, the side chain of Thr312 is packed within a tight loop, where additional bulk at position 312 likely distorts the shape of the loop, possibly causing protein misfolding. Indeed, while T312A was tolerated, T312L and T312V were lethal to the virus. T312L introduces a bulkier side chain, which likely disrupts the loop structure and therefore lethal to the virus, whereas T312V removes a polar hydroxyl group that also appears necessary for virus viability. In contrast, the side chain of Ile353 is fully exposed on the ubiquitin interaction surface. In other words, the side chain of this residue does not pack against or otherwise support any part of the PLP2 structure, therefore all side chain substitutions examined at this position were tolerated (T353Ala, Arg, Ser, Thr, Trp).

Moreover, the EAV PLP2 crystal structure can now be used to explain the results of substitutions made to the PLP2 domain by Sun et al (2010). For example, Cys429Ala, and His498Ala substitutions yielded non-viable virus since these residues comprise catalytic residues of the active site; however, Asp458Ala, while producing viable virus, had no effect of NF-KB activation, since according to the EAV PLP2 structure, only the main chain carbonyl group of at this position interacts with ubiquitin. Thus, with the exception of proline perhaps, side chain substitutions at this position would not affect the catalytic function of PLP2. Ser462Ala however also yielded viable virus with slightly reduced ability to suppress Ub-dependent NFκB activation (2-fold). Based on the EAV PLP2 structure, a polar residue at this position, such as Ser (SD-0180 PLP2) or Asp (EAV PLP2) is within hydrogen-bonding distance of Arg74 of ubiquitin, which is very close to the PLP2 active site. Mutations at this site while suppressing DUB activity could also suppress polyprotein processing, as evidenced by the reduced viral titer of the Ser462Ala compared to the Asp458Ala mutant. A third viable mutation created by Sun et al (Asp465Ala) exists within helix 2 at a position would not allow the residue to interact directly with ubiquitin. This residue appears important for packing interactions within the three-helix bundle of the PLP2 domain and thus while this mutation did affect NFκB activation, it had the greatest negative effect on virus titer, likely because disruption of the helical bundle adversely affects the overall stability of the PLP2 domain.

In addition to side chain substitutions (point mutations generated by site directed mutagenesis), deletions and/or insertions of a residue or residues within regions of the PLP2 domain that comprise the ubiquitin interactions surface could be employed to specifically disrupt DUB and deISGylating activity of the PLP2 domain. For example, insertion of additional residues within the sequence 479-484 of PRRSV strain Lelystad (487-492 of VR-2332, 313-318 of EAV) would introduce additional bulk on the enzyme surface at the ubiquitin interaction surface, thereby disrupting ubiquitin and ISG15 binding, without affecting the active site region and thus polyprotein processing by the PLP2 domain. This strategy of inserting or deleting residues to distort the ubiquitin interaction surface could be employed at any site within the PLP2 domain that is indicated above as amenable to mutation. Preferably, the strategy of inserting or deleting residues is applied to the PLP2 domain at any of consensus positions 296-297 and/or 303-306 and/or 309-319 and/or 326-330 and/or 343-355 according to the EAV numbering as depicted in FIG. 3.

More preferably, this strategy is applied to the regions of the PLP2 domain boxed by the thick lines in FIG. 3.

It is generally known that spontaneous random mutations do happen in nature, and this means that a mutation that is deliberately made in order to obtain a virus according to the invention may undergo a further, spontaneous, mutation. In a worst case scenario, this mutation leads to a reversion of a virus according to the invention to a virus that no longer shows a decreased DUB/deISGylating activity. It is one of the advantages of the present invention that several locations are now identified in which mutations leading to a decreased DUB/deISGylating activity can be made. This means that it is now possible to make not just one mutation, but two or more mutations in the regions as identified. Such mutants are even less prone to reversion, because the already low chances of a reversion mutation taking place are even further decreased.

Therefore, a most preferred replication-competent Arterivirus according to the invention comprises at least 2 mutations, each of which contributes to a decreased DUB/deISGylating activity. It is emphasized that two consecutive mutations at the nucleotide level, together leading to a mutation in a single amino acid are in this respect also considered to be comprised in the definition of a replication-competent Arterivirus according to the invention comprising at least 2 mutations. An example of such mutation is the EAV I353R mutant described above.

Figure 5:
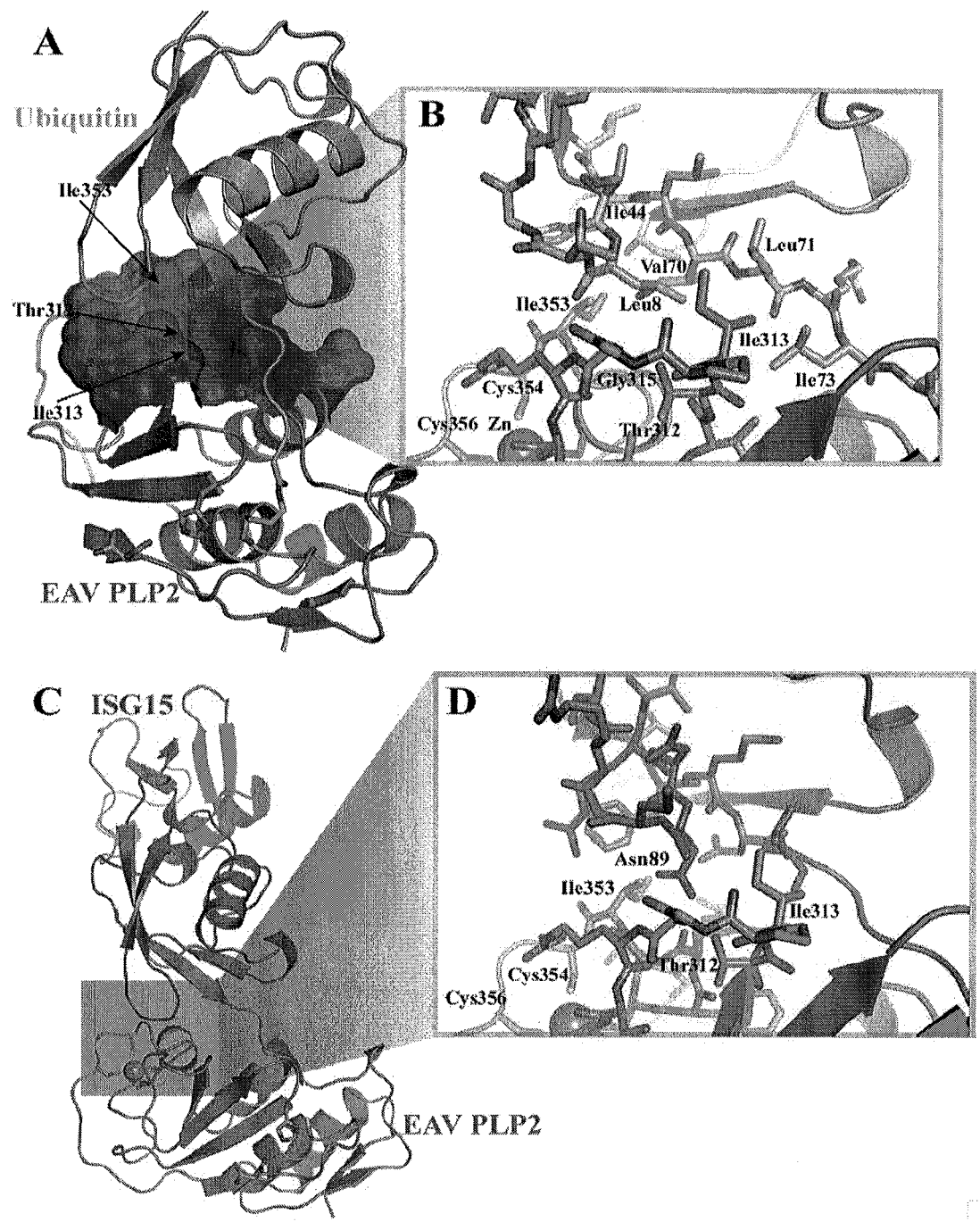

Merely as an example of how to use the information of the 3D-structure to make mutations that lead to viruses according to the invention: on the basis of the crystal structure (FIG. 5A, B) and a comparative molecular model of the PLP2 domain bound to ISG15 (FIG. 5C, D), the following can be seen: Ile353 is located at the C-terminal end of helix α3 next to C4 (Cys354) of the zinc coordination site. It projects directly into the Ile44 patch of Ub where it makes extensive van der Waals interactions with Ile44, Val70 and Leu8 of Ub. Thr312 and Ile313 are located closer to the active site, where they make additional hydrophobic interactions with residues Leu8, Leu71 and Leu73 of Ub. Thr312 makes a critical hydrogen bonding interaction with Asn89 of ISG15 (FIG. D).

On the basis of this information, a variety of single, double and triple mutations has now been made at three key positions (Ile353, Thr312 and Ile313) within the PLP2 domains' Ub-binding site.

An overview of the various mutations made is given in table 1, where the amino acid sequences shown are as follows: wild-type [SEQ ID NO: 13]; C270A/H332A [SEQ ID NO: 14]; T312A [SEQ ID NO: 15]; T312L [SEQ ID NO: 16]; T312V [SEQ ID NO: 17]; I353A [SEQ ID NO: 18]; I353R [SEQ ID NO: 19]; I353S [SEQ ID NO: 20]; I353W [SEQ ID NO: 21]; T312A/I313V [SEQ ID NO: 22]; T312A/I313V/353A [SEQ ID NO: 23]; T312A/I313V/353R [SEQ ID NO: 24]; and T312A/I313V/353W [SEQ ID NO: 25].

TABLE 1

| Amino acid | 261 | 270 | 312 | 332 | 353 | 386 |
|---|---|---|---|---|---|---|
| Wild-type | GYNPPGDGACGYSCLAF..25..PQLSPTFTVTIPGGRVCSNAKYAMICDKQHMRVKRAKGVGLCLDESCFRGICNCQRMS..20..FGNVRV | | | | | |
| C270A/H332A | ---------A----------------------------------A---------------------------------- | | | | | |
| T312A | ------------------------------A---------------------------------------------- | | | | | |
| T312L | ------------------------------L---------------------------------------------- | | | | | |
| T312V | ------------------------------V---------------------------------------------- | | | | | |
| I353A | ------------------------------------------------------A-------------------- | | | | | |
| I353R | ------------------------------------------------------R-------------------- | | | | | |
| I353S | ------------------------------------------------------S-------------------- | | | | | |
| I353W | ------------------------------------------------------W-------------------- | | | | | |
| T312A/I313V | ------------------------------AV--------------------------------------------- | | | | | |
| T312A/I313V/I353A | ------------------------------AV----------------------A-------------------- | | | | | |
| T312A/I313V/I353R | ------------------------------AV----------------------R-------------------- | | | | | |
| T312A/I313V/I353W | ------------------------------AV----------------------V-------------------- | | | | | |

Figure 8:
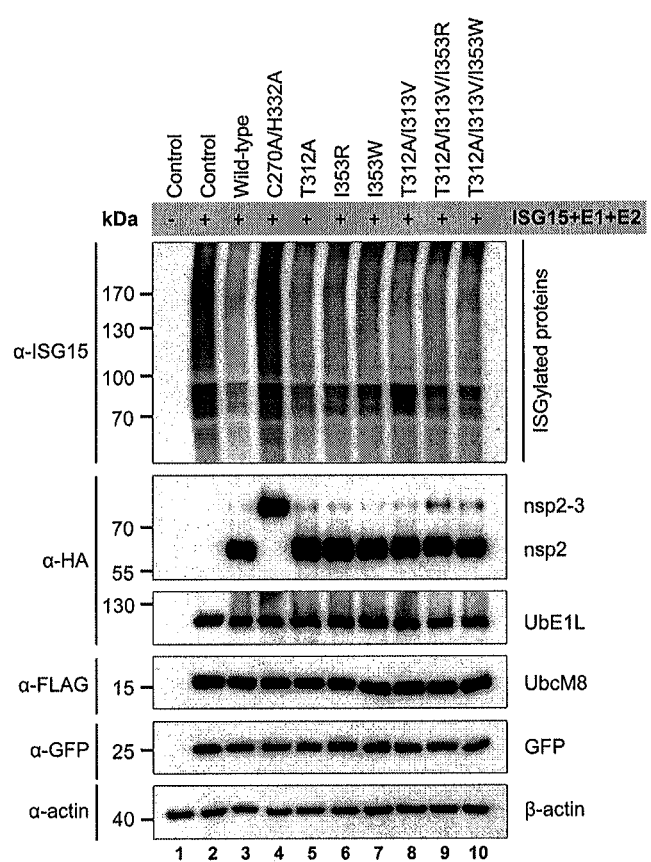

Before proceeding to infection experiments with recombinant viruses carrying these mutations, the inventors used two easy to use in vitro tests that allow for the fast screening of PLP2 mutants. These two tests are described below and details are provided in the Examples section and the results are shown in table 1.

The first test is based upon the fact that it is not necessary to try and produce a recombinant mutant virus carrying a mutation in the PLP2 domain through reverse genetics, followed by launching that virus in a cell culture system in order to test for its replication competence. Replication competence, in the context of these PLP2 experiments basically relies on the capability of a mutant PLP2 domain to perform nsp2/nsp3 cleavage and this can easily be tested in an in vitro system. The inventors used ectopic expression of the PLP2 domain and an in vitro assay to characterize the effect of various mutations at the above-mentioned positions on EAV replicase polyprotein processing and DUB/deISGylating activities. To this end, mutations were introduced into a mammalian expression vector encoding a self-cleaving nsp2-3 polyprotein carrying an N-terminal HA tag. Upon expression of wild-type nsp2-3 in HEK293T cells, PLP2 mediated cleavage of the nsp2/nsp3 junction (FIG. 6A). As expected, a PLP2 active site mutant (C270A/H332A) did not display any processing of the nsp2/nsp3 site and solely produced the nsp2-3 precursor (FIG. 6A). Seven single site mutants, in which the Ub-binding site was targeted by replacement of Thr312 or Ile353, displayed wild-type levels of nsp2/nsp3 cleavage, suggesting that polyprotein processing is not notably affected by these mutations (FIG. 6A). In addition, combinations of mutations at positions Thr312, Ile313, and Ile353 were tested, with essentially similar results (FIG. 6A). Longer exposure times did reveal some nsp2-3 precursor protein, even in the case of wild-type PLP2, but this amount only marginally increased when two or three mutations were combined (FIG. 7B, 8).

The second test is based upon the fact that it's not necessary to make a replication-competent recombinant Arterivirus having a mutation in the PLP2 domain, in order to test for a decreased DUB/deISGylating activity of such mutated PLP2. The effect of mutations on PLP2 DUB activity can be tested by transfecting mammalian cells with plasmids encoding nsp2-3 carrying wild-type or mutant PLP2 combined with a plasmid expressing FLAG-tagged Ub. Ectopic expression of FLAG-Ub leads to FLAG-tagged ubiquitination of a wide range of cellular targets, which can be visualized by Western blot analysis using an anti-FLAG antibody. As expected, expression of wild-type PLP2 strongly decreased the accumulation of Ub-conjugates, while expression of the active site mutant had a negligible effect (FIG. 6B). A selection of PLP2 mutants displaying the most pronounced reduction of DUB activity is presented in FIG. 6B. These Ub-binding site mutants displayed varying degrees of DUB activity, with phenotypes ranging between that of wild-type and the active site mutant (FIG. 6B). A similar experiment was used to assess the effect of these mutations on the deISGylating activity of PLP2. For this assay, mammalian cells were co-transfected with a combination of plasmids encoding ISG15 and the E1 (UbE1L) and E2 (UbcM8) enzymes essential for its conjugation, resulting in the ISGylation of a population of cellular proteins which can be visualized on Western blot using an anti-ISG15 antibody (FIG. 8). Again, expression of wild-type PLP2 strongly decreased the accumulation of ISGylated proteins (FIG. 8), while expression of the active site mutant did not (FIG. 8). It should be noticed, that the effect of mutations on the deISGylating activity of the PLP2 domain is more modest than their effect on DUB activity (FIG. 8).

An in vitro assay is performed to provide a more detailed analysis of the effect of mutations in PLP2 on activity towards Ub, ISG15, and an RLRGG-peptide substrate that represents the C-terminal tail of Ub or ISG15 that enters the active site of PLP2. For this assay, the inventors focused on mutants I353R and T312A/I313V/I353R, since these showed a pronounced effect on DUB activity in the cell culture-based assay, displayed a level of inhibition of IFN-β promoter activity similar to the active site mutant (described below), and yielded workable titers upon launching of the mutated virus in BHK-21 cells (described below).

The kinetics of peptidase enzymes follow the Michaelis-Menten (MM) equation:

$$\frac{d[P]}{dt} = \frac{k_{cat}[E][S]}{K_m + [S]}$$

In which [P] is the concentration of product, t is time, [S] is the concentration of substrate, [E] is the total concentration of enzyme and $k_{cat}$ and $K_m$ are the Michaelis parameters. The effects of amino acid point mutations on enzyme activity are best described by the how they affect the specificity of the enzyme as described by the ratio $$\frac{k_{cat}}{K_m}.$$

Normally the $k_{cat}$ and $K_m$ parameters are obtained separately from full-fledged Michaelis-Menten analysis. However, the ratio $$\frac{k_{cat}}{K_m}$$

can also be independently and accurately obtained from integrating the MM equation at low substrate concentrations:

$$\frac{d[P]}{dt} \approx \frac{k_{cat}[E][S]}{K_m} \Rightarrow [P] = [P]_\infty \left(1 - e^{-\frac{k_{cat}[E]}{K_m}t}\right) \quad (1)$$

The equation above can be used to quantify PLP2 activity in vitro using the fluorescent labelled substrates ubiquitin-aminomethylcoumarin (Ub-AMC), ISG15-aminomethylcoumarin (ISG15-AMC) or the C-terminal peptide motif of these substrates, RLRGG-AMC (Boston Biochem). PLP2 removes AMC from these substrates. The liberated AMC has a much higher fluorescence quantum yield than when it is coupled to Ub, ISG15 or the RLRGG peptide, and it thereby provides a fluorescence signal that is proportional to PLP2 activity. By comparing the activity of PLP2 mutants against Ub-AMC or ISG15-AMC (which require the ubiquitin interaction surface) versus their activity against RLRGG-AMC (which binds to the active site region only), PLP2 mutants with a selective reduction in DUB or deISGylating activity can be identified.

Since Ub-AMC and ISG15-AMC exhibit relatively poor solubility in water, complete MM analysis is difficult. Alternatively, equation 1 provides a useful method to circumvent solubility issues and determine $$\frac{k_{cat}}{K_m}$$

in a rapid and reliable fashion. Because the product fluorescence is proportional to its concentration, the evolution of product fluorescence over time proceeds according to the following modification of equation-1 at low substrate concentrations:

$$F = A_\infty \left(1 - e^{-\frac{k_{cat}[E]}{K_m}t}\right) \quad (1a)$$

Where F is the measured fluorescence and $A_\infty$ is a constant parameter. Thus, the time-profile of the fluorescence evolved after PLP2 has been added to a solution containing AMC-labelled substrate at a concentration significantly below the Km can be used to determine $$\frac{k_{cat}}{K_m}.$$

The Examples section provides ample examples of replication-competent Arteriviruses having a decreased DUB/deISGylating activity due to a mutation in the PLP2 domain of the non-structural protein nsp2.

The skilled person who wants to make additional Arteriviruses having a decreased DUB/deISGylating activity due to a mutation in the PLP2 domain of nsp2, may use the in vitro tests as discussed above for determining nsp2/nsp3 protease activity and the DUB/deISGylation activity, as described above and as described in a detailed manner in the Examples, for the fast screening of PLP2 mutants.

As mentioned above the crystal structure of the PLP2 domain bound to ubiquitin could be determined due to the fact that such crystals could now for the first time be made in a stable form.

The formation of such crystals was possible through the mixing of ubiquitin to a purified nsp2 fragment that comprises a PLP2 domain, under conditions allowing covalent binding of ubiquitin to the PLP2 domain in order to form a PLP2-ubiquitin complex. The PLP2 domain may be the domain as such (e.g. the amino acids from position 261-392 of the EAV nsp2), or it may comprise the PLP2 domain and a further part of the nsp2 protein.

The same approach applies to the formation of such crystals through the mixing of ISG15 to a purified nsp2 fragment that comprises a PLP2 domain, under conditions allowing covalent binding of ISG15 to the PLP2 domain in order to form a PLP2-ISG15 complex.

Therefore, another embodiment of the present invention relates to a PLP2-ubiquitin complex comprising ubiquitin and at least the PLP2 domain of nsp2 of an Arterivirus, wherein said PLP2 domain is covalently bound to said ubiquitin, or a PLP2-ISG15 complex comprising ISG15 and at least the PLP2 domain of nsp2 of an Arterivirus, wherein said PLP2 domain is covalently bound to said ISG15.

In a preferred form of this embodiment the Arterivirus is selected from the group of viruses consisting of EAV and PRRSV.

Again another embodiment of the present invention relates to live attenuated vaccines for the protection of mammals against Arteriviral infection, characterized in that such vaccines comprise a replication-competent Arterivirus according to the invention, and a pharmaceutically acceptable carrier.

As a starting material for making a live attenuated vaccine according to the invention, either a wild-type or a live attenuated viral strain may be used. Methods for the attenuation of viruses, e.g. through serial passage over different cell lines have been extensively described in the art. They are well-known to the skilled person.

However, for the skilled person in need of a vaccine for PRRSV or EAV according to the invention who wants to start with an attenuated virus strain, there is in principle no need to develop new live attenuated Arteriviruses. Live attenuated PRRSV and EAV have been described in the literature and they are commercially available. Therefore, such viruses can form a very suitable starting material for the skilled person wanting to develop a live attenuated vaccine according to the invention.

An overview of commercially available live modified PRRSV-vaccines, their characteristics and their producers is given i.a. by Murtaugh, M. P. and Genzow, M. (Vaccine 29: 8192-8204 (2011)).

An overview of live modified EAV-vaccines is given i.a. by McCollum, W. H. (American Journal of Veterinary Research 47: 1931-1934 (1986)), and by Summers-lawyer, K. A. et al., (Journal of Equine Veterinary Science Volume 31: 129-138 (2011)). A live attenuated EAV virus has i.a. been licensed in the USA.

Usually, the vaccine according to the invention will be administered through the parenteral route. Preferably, the vaccine will be administered intramuscularly.

A suitable amount of a virus according to the invention in a vaccine would range between $10^2$ and $10^8$ TCID$_{50}$ depending on the level of attenuation of the virus used. The literature cited above and the knowledge in the art with regard to EAV and PRRSV vaccination gives the skilled person ample guidance to determine the amount of virus needed. In case a vaccine strain is based upon an existing, commercially available virus strain comprising an attenuating deletion, the manufacturer's instructions would provide good guidance regarding the amount of virus to be used. As a rule of thumb, for live attenuated viruses, an amount of between $10^4$ and $10^6$ TCID$_{50}$ would be considered a very suitable amount of virus.

Next to diseases caused by Arteriviruses, horses and swine often suffer from a variety of other viral, parasitic and bacterial diseases. For this reason they are frequently vaccinated against such diseases.

Therefore there are good reasons from a point of animal welfare, ease of use and cost saving to combine several vaccines and administer such combination vaccines in one single administration. Thus, a preferred form of this embodiment relates to a vaccine according to the invention, characterized in that said vaccine comprises an additional immunogen of a virus or micro-organism pathogenic to the animal to be vaccinated, an antibody against said immunogen or genetic information encoding an immunogen of said virus or micro-organism.

Amongst the most frequently seen examples of viruses/micro-organisms pathogenic to swine are *Brachyspira hyodysenteriae*, African Swine Fever virus, Nipah virus, Porcine Circovirus, Porcine Torque Teno virus, Pseudorabies virus, Porcine influenza virus, Porcine parvo virus, Porcine Epidemic Diarrheal virus (PEDV), Foot and Mouth disease virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

Thus a more preferred form of this embodiment relates to a vaccine according to the invention, characterized in that said virus or micro-organism pathogenic to swine is selected from the group consisting of *Brachyspira hyodysenteriae*, African Swine Fever virus, Nipah virus, Porcine Circovirus, Porcine Torque Teno virus, Pseudorabies virus, Porcine influenza virus, Porcine Epidemic Diarrheal virus (PEDV), Foot and Mouth disease virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

Amongst the most frequently seen examples of viruses/micro-organisms pathogenic to equines are Equine Influenza virus, *Clostridium tetani*, Equine Herpesvirus 1 and Equine Herpesvirus 4. Thus an equally more preferred form of this embodiment relates to a vaccine according to the invention, characterized in that said virus or micro-organism pathogenic to equines is selected from the group consisting of Equine Influenza virus, *Clostridium tetani*, Equine Herpesvirus 1 and Equine Herpesvirus 4.

A pharmaceutically acceptable carrier can be, or may include, stabilizers, diluents and buffers. Suitable stabilizers are for example SPGA, carbohydrates (such as dried milk, serum albumin or casein) or degradation products thereof. Suitable buffers are for example alkali metal phosphates. Diluents include water, aqueous buffers (such as buffered saline), alcohols and polyols (such as glycerol).

Vaccines in general, but especially vaccines comprising live attenuated viruses must be stored at low temperature, or they have to be in a freeze-dried form. Freeze-dried vaccines can be kept under moderate cooling conditions or even at room temperature. Often, the vaccine is mixed with stabilizers, e.g. to protect degradation-prone proteins from being degraded, to enhance the shelf-life of the vaccine, or to improve freeze-drying efficiency. Useful stabilizers are i.a. SPGA, carbohydrates e.g. sorbitol, mannitol, trehalose, starch, sucrose, dextran or glucose, proteins such as albumin or casein or degradation products thereof, and buffers, such as alkali metal phosphates.

Therefore, preferably, a vaccine according to the invention is in a freeze-dried form.

In addition, the vaccine may be suspended in a physiologically acceptable diluent. Such buffers can e.g. be sterile water, a buffer and the like.

It goes without saying, that diluents and compounds for emulsifying or stabilizing viruses are also embodied in the present invention.

Still another embodiment of the invention relates to a replication-competent Arterivirus according to the invention for use as a medicament.

Again another embodiment of the invention relates to a replication-competent Arterivirus according to the invention for use in a vaccine.

And again another embodiment of the invention relates to a replication-competent Arterivirus according to the invention for use in the prophylaxis of Arterivirus infection in a mammal.

EXAMPLES

Example 1

Plasmids, cells and antibodies. For bacterial expression of EAV PLP2, a cDNA fragment encoding residues 261-392 of EAV pp1a and an in-frame C-terminal $HIS_6$ purification tag was inserted downstream of a Ub fusion partner in the pASK3 vector (Gohara et al., 1999), yielding plasmid pASK3-ePLP2. A mammalian expression construct encoding an EAV nsp2-3 polyprotein was made by cloning residues 261-1064 of EAV pp1a in-frame with an N-terminal HA tag in the pcDNA3.1 vector (Invitrogen). All mutants were engineered by site-directed mutagenesis using Pfu DNA polymerase (Fermentas). Primer sequences are available upon request. All constructs were verified by sequence analysis. The following mammalian expression plasmids were described elsewhere: pLuc-IFN-β (Fitzgerald et al., 2003), pRL-TK (Promega), pEBG-RIG-I$_{(2CARD)}$ (Gack et al., 2007), pcDNA-eGFP (van Kasteren et al., 2012), pCMV-FLAG-Ub (Gack et al., 2009), pCAGGS-HA-mUbE1L, pCMV2-FLAG-UbcM8, and pCAGGS-V5-hISG15 (Versteeg et al., 2010).

HEK293T cells were cultured in Dulbecco's modified Eagle medium (Lonza) supplemented with 10% fetal bovine serum (FBS), and 2 mM L-glutamine. BHK-21 cells were cultured in Glasgow minimum essential medium (Lonza) supplemented with 5% FBS, 10% tryptose phosphate broth, and 10 mM HEPES (pH 7.4). Primary equine lung fibroblasts (ELF) were cultured in minimum essential medium (Lonza) supplemented with 10% FBS and grown on collagen-coated plastics. All culture media contained 100 U/ml of penicillin and 100 mg/ml of streptomycin.

The following commercially available antibodies were used: α-HA (ab18181; Abcam), α-FLAG (F3165; Sigma-Aldrich), α-GST (sc459; Santa Cruz), α-β-actin (A5316; Sigma-Aldrich), donkey-α-mouse-Cy3 (715-165-151; Jackson ImmunoResearch), and goat-α-rabbit-AL488 (A-11008; Invitrogen). The following antibodies were described elsewhere: α-hISG15 (clone 2.1) (Malakhov et al., 2003) and α-EAV N protein (clone 3E2) (MacLachlan et al., 1998). Rabbit antisera recognizing the EAV PLP2 domain and GFP were raised using recombinant proteins purified from *Escherichia coli*.

Purification and crystallization of the EAV PLP2 domain bound to Ub. *E. coli* BL21-Gold(DE3) cells were transformed with pASK3-ePLP2 and cultured to an optical density ($OD_{600}$) of 0.7 in LB medium at 37° C. The culture was then supplemented with 200 ng/ml of anhydrous tetracycline and incubated for 3 hrs at 28° C. with shaking to induce expression of the Ub-PLP2-$HIS_6$ fusion protein. The cells were pelleted and resuspended in ice-cold lysis buffer (20 mM MES pH 7, 500 mM NaCl, 10% glycerol, 5 mM imidazole pH 7.4, 0.5 mM TCEP) and lysed using a French pressure cell (AMECO). The lysate was clarified by centrifugation and loaded onto a Ni-NTA column (Qiagen) pre-equilibrated with lysis buffer. After washing with lysis buffer supplemented with 15 mM imidazole, recombinant PLP2 was eluted from the column using an equilibration buffer supplemented with 150 mM imidazole and exchanged into 50 mM Tris, pH 8.0, 300 mM NaCl and 5 mM DTT before storing at 4° C. The endogenous DUB activity of the PLP2 domain resulted in the efficient removal of the N-terminal Ub-tag from the fusion protein during expression in *E. coli*; therefore, affinity chromatography yielded highly pure PLP2 carrying a C-terminal $HIS_6$ purification tag only.

The mechanism-based suicide inhibitor $Ub_{(1-75)}$-3-bromopropylamine (Ub-3Br) was prepared according to Messick et al (Messick et al., 2008) and Borodovsky et al (Borodovsky et al., 2002) as described by James et al (James et al., 2011). Ub-Br3 was covalently bound to purified PLP2 by gently mixing the proteins in a 3:2 molar ratio for one hour at 37° C. The resulting PLP2-Ub complex was purified by gel filtration (Superdex 75) followed by anion exchange (Source 15Q) chromatography and then exchanged into 20 mM Tris, pH 8.0, 50 mM NaCl before concentrating to 10 mg/ml and storing at 4° C.

The PLP2-Ub complex was crystallized by hanging-drop vapor diffusion at 10 mg/ml in mother liquor consisting of 100 mM MES pH 6.2, 18% PEG 20,000. Crystals were flash-cooled and stored in liquid nitrogen after sweeping them through mother liquor supplemented with 20% glycerol.

X-ray data collection and crystal structure determination. X-ray diffraction data for a multiwavelength anomalous dispersion (MAD) experiment were collected at the Canadian Light Source (beam line 08ID-1). Data were collected at three different wavelengths over the absorption edge of zinc from a single crystal of the PLP2-Ub complex held at 100K in a $N_2$ (g) stream. The data were processed using MOSFLM and SCALA (Collaborative Computational Project Number 4, 1994) and structure factor phases were determined using phenix.autosol (Adams et al., 2010). Initial phases generated by SOLVE were improved by density modification using RESOLVE within the PHENIX package. After reserving a random subset of reflections for cross-validation using the free R-factor (Brunger, 1992), a model was built using phenix.autobuild (Adams et al., 2010) and manually completed and refined using COOT (Emsley and Cowtan, 2004) and phenix.refine (Adams et al., 2010).

Comparative Molecular Modeling of the PLP2 Domain from PRRSV Strains Lelystad and VR2332

Comparative molecular models of the PLP2 domain from PRRSV strains Lelystad and VR2332 were built using the program MODELLER 9.10 (Eswar, N. et al., 2006) based on a multiple sequence alignment of the full-length nsp2 sequences of PRRSV strains Lelystad, VR2332 and GM2, and the sequence of the crystallized PLP2 domain from EAV Bucyrus (nsp2 residues 261-387) (FIG. 3). The multiple alignment was generated using the ClustalW algorithm within the Geneious Pro 5.1.7 software package. Modeled residues for Lelystad (420-555) and VR2332 (428-566) were those that aligned to crystal structure of the EAV Bucyrus PLP2 domain. Loop structures unique to the Lelystad and VR2332 PLP2 domains (i.e. not present within the EAV PLP2 crystal structure) were optimized using the 'loopmodel' subroutine with MODELLER 9.10. Models of the Lelystad and VR2332 PLP2 domains bound to ubiquitin were generated by superposing the models of these PLP2 domains onto the PLP2 domain of the crystallographic complex of the EAV PLP2 domain bound to ubiquitin using the program PyMOL (DeLano W L (2002) The PyMOL Molecular Graphics System (DeLano Scientific, Palo Alto, Calif., USA.)) The alignment revealed that the PRRSV models could readily accommodated ubiquitin in the same binding orientation and C-terminal tail conformation as observed when bound to the EAV PLP2 crystal structure. No serious structural clashes between ubiquitin and the PRRSV models were observed, including within the tight groove leading to the enzyme active site that binds the C-terminal RLRGG of ubiquitin. The zinc atom was added to the Lelystad and VR2332 PLP2 models using the same superposition, revealing that cysteine residues within these models cluster about the superposed zinc atom and providing strong evidence for a zinc finger motif to be present within this region of these PRRSV PLP2 domains similarly to that observed for the EAV PLP2 crystal structure.

Cell-culture based assays. To assess nsp2/nsp3 cleavage by the various PLP2 mutants, HEK293T cells were grown to 80% confluence in 10 cm² wells and transfected using CaPO₄ with 4 μg plasmid DNA encoding nsp2-3 containing wild-type or mutant PLP2. After 16 h at 37° C., cells were lysed in 2× Laemmli Sample Buffer (2×LSB; 250 mM Tris, 2% SDS, 20% glycerol, 0.01% bromophenol blue, 2 mM DTT, pH 6.8). Samples were loaded on SDS-polyacrylamide gels, which were blotted to Hybond-P polyvinylidene difluoride membranes (GE Healthcare) using a semi-dry transfer cell (Bio-Rad). After incubation with the appropriate antibodies, protein bands were visualized using the Amersham ECL Plus detection reagent (GE Healthcare).

To assess the DUB activity of the various PLP2 mutants, HEK293T cells were grown to 80% confluence in 4 cm² wells and transfected using CaPO₄ with a combination of plasmids encoding FLAG-Ub (0.25 μg), GFP (0.25 μg), and nsp2-3 containing wild-type or mutant PLP2 (1.5 μg). After 16 h at 37° C., cells were lysed in 2×LSB and analyzed by SDS-PAGE as described above.

To assess deISGylation activity of the various mutants, HEK293T cells were grown to 80% confluence in 4 cm² wells and transfected using CaPO₄ with a combination of plasmids encoding hISG15 (0.75 μg), HA-mUbE1L (0.25 μg), FLAG-UbcM8 (0.25 μg), GFP (0.25 μg) and nsp2-3 containing wild-type or mutant PLP2 (0.5 μg). After 48 h at 37° C., cells were lysed in 2×LSB and analyzed by SDS-PAGE as described above.

Luciferase-based IFN-β promoter activity assay. HEK293T cells, grown to 80% confluence in 2 cm² wells, were transfected in quadruplicate with a combination of plasmids encoding firefly luciferase under control of the IFN-β promoter (50 ng), renilla luciferase (5 ng), RIG-I $_{(2CARD)}$ (25 ng) and nsp2-3 containing wild-type or mutant PLP2 (500 ng) using Lipofectamine-2000 (Invitrogen). The total amount of DNA used for transfection was adjusted to 1 μg per well by the addition of the appropriate amount of empty vector. After 12 h at 37° C., three out of four wells were lysed in 100 μl passive lysis buffer (Promega), and samples were assayed for luciferase activity using the Dual-Luciferase reporter assay system (Promega) on a Mithras LB 940 multimode reader (Berthold Technologies). The remaining wells from each of three independent experiments were lysed in 2×LSB, mixed in a 1:1:1 ratio and analyzed by SDS-PAGE as described above.

An unpaired two-tailed Student's t test was used to determine the statistical significance of the results, which were obtained in three independent experiments. P values<0.05 were considered to be statistically significant.

In vitro PLP2 Domain Activity Assay

Examples of experimentally determined values of $$\frac{k_{cat}}{K_m}$$

for the cleavage of Ub-AMC and RLRGG-AMC by a wild-type EAV PLP2 domain and a variant containing a single point mutation on the ubiquitin interaction surface (Ile353Arg) are shown in Table X. Steady-state fluorescence spectra were measured on a Fluorolog-3 Horiba Jobin Yvon spectrofluorometer (Edison, N.J.). The sample was held in a 10×3 mm² disposable cuvette. The data were analyzed with Sigma Plot (Point Richmond, Calif.) software. Measurements were performed at room temperature in 50 mM tris at 150 mM ionic strength (NaCl) buffer pH 8 from Sigma (St-Louis, Mo.). Substrate concentrations were kept at 50 μM and 200 nM for the RLRGG-AMC and Ub-AMC substrates respectively, while the enzyme concentrations were used at final concentrations between 1.7-2.6 μM for the RLRGG-AMC substrate and 116-174 nM for the Ub-AMC substrate. The samples were excited with 360 nm light and the time-dependent emission was collected at 460 nm.

The excitation and emission silts were set to a 3 nm bandpass. Values of $$\frac{k_{cat}}{K_m}$$

measured for the wild-type and mutant are given Table 3.

As can immediately be seen from this table, the $k_{cat}/K_M$ value for RLRGG-AMC of the wild-type virus and the mutant I353R is comparable, whereas the $k_{cat}/K_M$ value for Ub-AMC of the mutant I353R is 20 times lower than that of the wild-type virus.

TABLE 3

Experimental $k_{cat}/K_M$ values for the wild-type and I353R mutant EAV PLP2 enzymes determined with respect to the RLRGG-AMC and Ub-AMC substrates.

| Enzyme | Substrate | |
|---|---|---|
| | RLRGG-AMC $k_{cat}/K_M$ | Ub-AMC $k_{cat}/K_M$ |
| Wild-type | 48 ± 8 M⁻¹s⁻¹ | 21000 ± 2000 M⁻¹s⁻¹ |
| I353R | 71 ± 8 M⁻¹s⁻¹ | 1100 ± 100 M⁻¹s⁻¹ |

Reverse genetics. Mutations in the EAV PLP2-coding sequence were engineered in an appropriate shuttle vector by site-directed mutagenesis using Pfu DNA polymerase (Fermentas) and subsequently transferred to pEAN551/AB, which is a derivative of EAV full-length cDNA clone pEAN551 carrying additional (translationally silent) AflII and BspEI restriction sites (Posthuma et al., 2008). The virus derived from pEAN551/AB was used as wild-type control in all experiments. All constructs were verified by sequence analysis.

In vitro RNA transcription from XhoI-linearized wild-type or mutant EAV full-length cDNA clones was performed using the mMESSAGE mMACHINE T7 Kit (Ambion). Five μg of in vitro synthesized EAV RNA was electroporated into 5.0^10⁶ BHK-21 cells using the Amaxa Cell Line Nucleofector Kit T and the program T-020 of the Amaxa Nucleofector (Lonza) according to the manufacturer's instructions. Cells were resuspended in the appropriate medium, seeded in 75 cm² flasks and incubated at 39.5° C. Virus-containing supernatants were harvested at 24 h post transfection and titers were determined by plaque assay on equine lung fibroblast cells as described before (Nedialkova et al., 2010).

To verify the presence of the correct mutations, RNA was isolated from virus-containing supernatants using the QIAamp Viral RNA Mini Kit (Qiagen) and converted to DNA using RevertAid H Minus reverse transcriptase (Fermentas) and random hexameric primers. The region of the PLP2 domain encoding the mutations was subsequently PCR amplified using Pfu DNA polymerase (Fermentas) and sequenced.

Quantitative real-time PCR. Confluent equine lung fibroblast cells were infected with wild-type or mutant EAV at an m.o.i. of 0.25 and incubated at 37° C. At 20 and 24 h p.i., cell lysates were harvested in TriPure Isolation Reagent (Roche). After the addition of chloroform, the aqueous phase was mixed in a 1:1 ratio with buffer RA1 of the Nucleospin RNA II kit (Macherey-Nagel) and RNA was isolated as per manufacturer's instructions. Isolated RNA was subsequently used as a template for cDNA synthesis using RevertAid H Minus reverse transcriptase (Fermentas) and oligo(dT)20 primer. Finally, samples were assayed by quantitative real-time PCR (qRT-PCR) on a CFX384 Touch Real-Time PCR detection system (BioRad) using iTaq SYBR Green Supermix with ROX (BioRad). Primers targeting equine GAPDH, Actin-β, IFN-β, and the EAV genome were designed using Primer3 (Rozen and Skaletsky, 1998) and sequences are given in Table 2. The real-time PCR program was followed by a melting-curve analysis, to verify specificity of the reaction. Results were quantified using the standard curve method and normalized against the geometric mean of the relative quantities of GAPDH and Actin-β.

EAV PLP2 active site. Blue density is a maximum-likelihood weighted $2F_o$-$F_c$ map contoured at 1.0σ. The cysteine nucleophile (Cys270) is covalently linked to Ub via the 3NC linker, which replaces Gly76 of Ub. Asn263, which orients the imidazole ring of His332 occurs in two alternate conformations. D) Superposition of EAV PLP2 (violet), CCHFV OTU (green) and yeast OTU1 (red). PLP2 shares a conserved core of two central helices and a four-stranded beta sheet with CCHFV OTU and yeast OTU1. E) Superposition of EAV PLP2 and CCHFV OTU complexed with Ub. Both enzymes grasp Ub in a similar orientation, with the C4 zinc finger motif of EAV PLP2 replacing the β-hairpin of CCHFV OTU. Topology diagrams for EAV PLP2, CCHFV OTU and yeast OTU1 are shown in panels F, G, and H, respectively. The region that is conserved amongst the enzymes is outlined (dashed box). The four cysteine residues coordinating the zinc atom in EAV PLP2 are shown as yellow circles. Structural images were prepared using PyMOL (DeLano, 2002).

FIG. 2: EAV PLP2 structure (based on PISA analysis). The grey area defines the ubiquitin interaction surface on the PLP2 enzyme (617 Å$^2$) that should be targeted to selectively disrupt DUB and ISGylating activity. The catalytic nucleophile cysteine 270 (C270) within the enzyme active site is

TABLE 2

| Target (Accession) | Forward primer (5'-3') | Reverse primer (5'-3') |
| --- | --- | --- |
| Equine GAPDH (NM_001163856) | TGCCGCCTGGAGAAAGCTGC | GAGGGCAATGCCAGCCCCAG |
| Equine Actin-β (NM_001081838) | CCACGCCATCCTGCGTCTGG | ACCGCTCGTTGCCGATGGTG |
| Equine IFN-β (NM_001099440) | AGGTGGATCCTCCCAATGGCCC | GGGGCAACGTTGAGGGGCTC |
| EAV genome (NC_002532) | CCGACCCGGTGTGACCGTTG | AAGGGTCGCGGGTGCCAATG |

FIG. 9 shows the results of the qPCR. In FIG. 9B, it can be seen that the amount of viral mRNA produced in primary equine lung cells infected with wild type virus, a single mutant (I353R) and a triple mutant (T312A/I313V/I353R) is practically equal. This shows that in these mutant viruses the replication level is practically unchanged compared to that of wild-type virus, indicating that the mutants are capable of polyprotein processing.

In FIG. 9A it can be seen that the induction of IFN beta mRNA is significantly higher in the mutants than in the wild-type virus. It can also be seen that the triple mutation has an even lower inhibitory effect on the induction of IFN beta than the single mutant. It is clear from this figure that indeed the mutants show a very significant decrease in DUB/deISGylation activity, which directly relates to a significant attenuation of the inhibitory effect on IFNbeta induction that the wild-type virus does display through its DUB/deISGylating activity. This indicates that mutant viruses according to the invention trigger a better cellular immune response than the wild-type versions, and thus indeed provide improved vaccines.

LEGEND TO THE FIGURES

FIG. 1: Structure of the EAV PLP2-Ub complex and superposition with yeast OTU1 and CCHFV OTU. A) Structure of EAV PLP2 (violet) bound to Ub (orange). B) Electron density for the C4 zinc finger motif. Blue density is a maximum-likelihood weighted $2F_o$-$F_c$ map contoured at 1.0σ. Green density about the zinc atom (grey) is a $F_o$-$F_c$ omit map contoured at 5.0σ. C) The catalytic triad of the covalently bound to the C-terminus of ubiquitin, resembling the acyl-enzyme intermediate step of the catalytic reaction.

FIG. 3: Multiple sequence alignment of EAV and PRRS sequences. This figure represents the structurally functional alignment for the Arteriviral PLP2 domain. EAV Bucyrus PLP2 X-ray structure NC 002532 [SEQ ID NO: 9]; PRRSV Lelystad nsp2 (aa 420-555) M96262 [SEQ ID NO: 10]; PRRSV VR-2332 nsp2 (aa 428-566) U87392 [SEQ ID NO: 11]; PRRSV GM2 nsp2 (aa 428-566) JN662424 [SEQ ID NO: 12].

FIG. 4: Structure models of PRRSV PLP2 domain based on the crystallographic structure of Arteriviral PLP2 domain bound to Ub. A) Molecular model of the PLP2 domain bound to ubiquitin from PRRSV strain Lelystad. B) Molecular model of the PLP2 domain bound to ubiquitin from PRRSV strain VR-2332. C) Molecular model of the PLP2 domain bound to ubiquitin from EAV strain Bucyrus. D) Table showing PRRSV PLP2 residues that are in place of residues Thr 312, Ile 313, Ile 353 of the EAV PLP2 domain.

FIG. 5: Ub-binding site of the EAV PLP2 domain and comparative model of ISG15 bound to the EAV PLP2 domain. A) EAV PLP2 (dark grey) bound to Ub (light gray), with the 612 $Å^2$ Ub-binding site shown as a surface. Residues targeted for mutational analysis to disrupt DUB and deISGylating activities are indicated by arrows. B) Close-up of the EAV PLP2-Ub binding interface. EAV PLP2 residue Ile353 forms van der Waals interactions with Ile44, Leu8, and Val70 of Ub, whereas residues Thr312 and Ile313 interact with a hydrophobic patch on Ub (formed by residues Leu8, Val70, Leu71, and Ile73) closer to the active site of PLP2. C) Comparative molecular model of the EAV PLP2 domain bound to ISG15. The model was constructed by superposing the C-terminal Ub-like domain of ISG15 (from PDB 1Z2M) onto the Ub molecule of the EAV PLP2-Ub complex. The model predicts that the EAV PLP2 domain binds ISG15 such that it can accommodate the additional bulk present on ISG15 that is absent in Ub. D) Close-up of the modeled EAV PLP2-ISG15 binding interface showing a hydrogen bonding interaction between residues Asn89 of ISG15 and Thr312 of the EAV PLP2 domain believed to be important for ISG15 binding.

Figure 6:
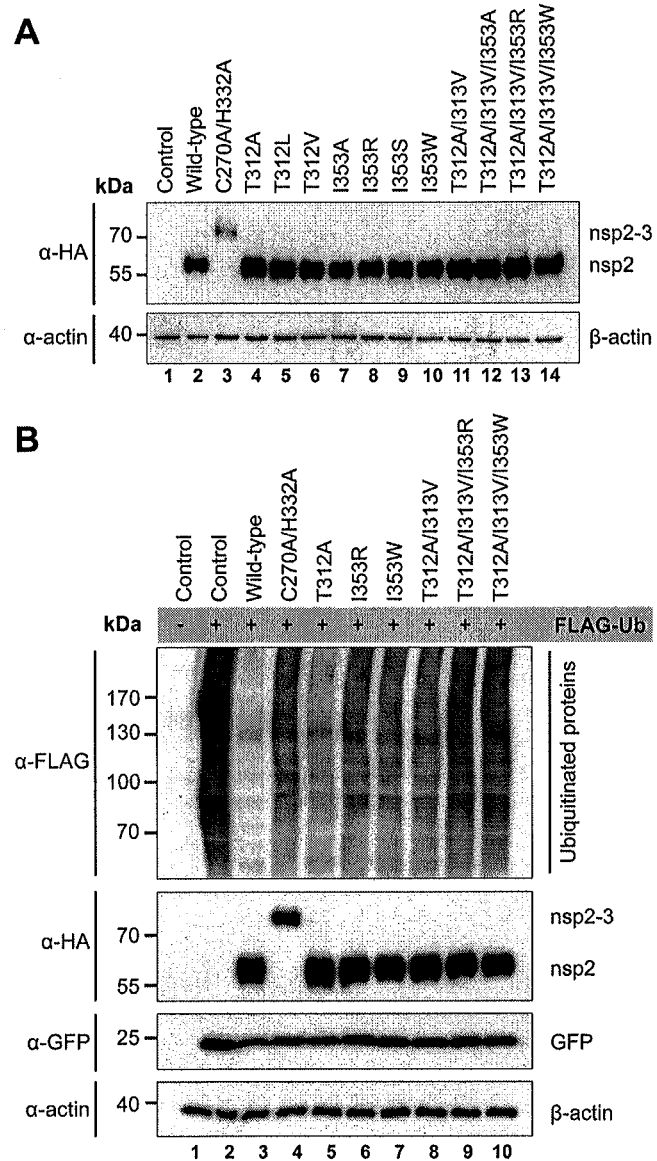

FIG. 6: Decoupling of the polyprotein processing and DUB activities of the EAV PLP2 domain.

A) HEK293T cells were transfected with plasmids encoding nsp2-3 containing wild-type or mutant PLP2. After 16 h at 37° C., cells were lysed and results were analyzed by Western blot. Proteolytic processing of the nsp2|3 junction by wild-type PLP2 resulted in the release of HA-tagged nsp2 from the nsp2-3 precursor. Except for mutant C270A/H332A, which is catalytically inactive (van Kasteren et al., 2012), all mutants displayed efficient processing of the nsp2|3 cleavage site.

B) HEK293T cells were transfected with a combination of plasmids encoding nsp2-3 containing wild-type or mutant PLP2 and FLAG-Ub. Expression of FLAG-Ub leads to FLAG-tagged ubiquitination of a wide range of cellular proteins, which can be visualized on Western blot using an anti-FLAG antibody. Expression of wild-type PLP2 strongly decreased ubiquitination, while expression of the C270A/H332A mutant did not. Ub-binding site mutants showed varying degrees of DUB activity, with phenotypes ranging between wild-type and the active site mutant.

Figure 7:
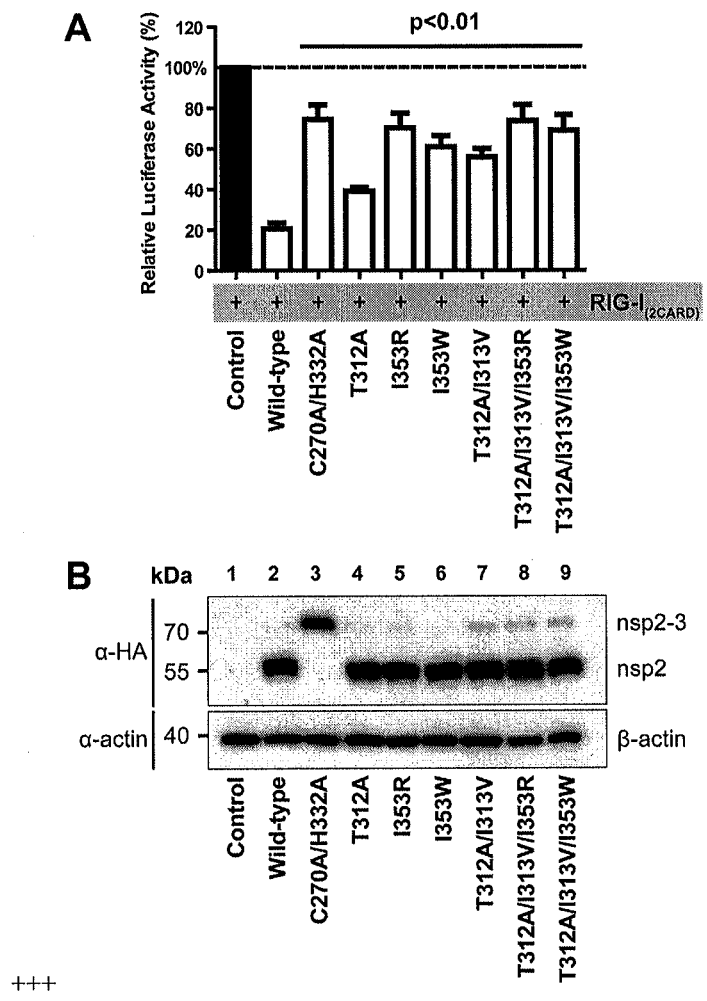

FIG. 7: PLP2 Ub-binding site mutations attenuate inhibition of IFN-β promoter activation.

A) Luciferase-based reporter assay to assess the effect of various PLP2 Ub-binding site mutations on inhibition of IFN-β promoter activity. HEK293T cells were transfected in quadruplicate with a combination of plasmids encoding firefly luciferase under control of the IFN-β promoter, renilla luciferase, RIG-I$_{(2CARD)}$, and nsp2-3 containing wild-type or mutant PLP2. Wild-type PLP2 strongly inhibited activation of the IFN-β promoter, while the active site mutant showed only minor inhibitory activity. Ub-binding site mutants showed varying degrees of inhibition. Data was obtained in three independent experiments and analyzed using an unpaired two-tailed Student's t test. Error bars represent standard deviation and p-values are relative to wild-type.

B) Lysates obtained from the remaining wells in each of three experiments described under A were mixed in a 1:1:1 ratio and analyzed by Western blot for the expression of nsp2-3.

FIG. 8: HEK293T cells were transfected with a combination of plasmids encoding nsp2-3 containing wild-type or mutant PLP2, ISG15, and E1 (UbE1L) and E2 (UbcM8) enzymes. Expression of ISG15 and its E1 and E2 enzymes results in the ISGylation of a population of cellular proteins, which can be visualized on Western blot using an anti-ISG15 antibody. Expression of wild-type PLP2 decreased ISGylation, while expression of the active site mutant did not. Ub-binding site mutations had only a mild effect on deISGylating activity.

FIG. 9: Quantitative real-time PCR. This figure shows the effect of several mutations in the PLP2 domain on viral growth (quantification of EAV genome in FIG. 9B) and on DUB/deISGylation activity (assayed by the quantification of IFNbeta mRNA induction as a result of the infections in FIG. 9A, which directly (reciprocally) correlates to the DUB-ISGylating activity).

REFERENCES

Adams, P. D., Afonine, P. V., Bunkoczi, G., Chen, V. B., Davis, I. W., Echols, N., Headd, J. J., Hung, L.-W., Kapral, G. J., Grosse-Kunstleve, R. W., McCoy, A. J., Moriarty, N. W., Oeffner, R., Read, R. J., Richardson, D. C., Richardson, J. S., Terwilliger, T. C., Zwart, P. H., 2010. PHENIX: a comprehensive Python-based system for macromolecular structure solution. Acta Crystallographica Section D 66, 213-221.

Akutsu, M., Ye, Y., Virdee, S., Chin, J. W., Komander, D., 2011. Molecular basis for ubiquitin and ISG15 cross-reactivity in viral ovarian tumor domains. Proc Natl Acad Sci USA 108, 2228-2233.

Arguello, M. D. and Hiscott, J., Cell Host & Microbe 2: 367-369 (2007).

Andreini, C., Bertini, I., Cavallaro, G., 2011. Minimal Functional Sites Allow a Classification of Zinc Sites in Proteins. PLoS One 6, e26325.

Behrends, C., Harper, J. W., 2011. Constructing and decoding unconventional ubiquitin chains. Nat Struct Mol Biol 18, 520-528.

Borodovsky, A., Ovaa, H., Kolli, N., Gan-Erdene, T., Wilkinson, K. D., Ploegh, H. L., Kessler, B. M., 2002. Chemistry-based functional proteomics reveals novel members of the deubiquitinating enzyme family. Chem Biol 9, 1149-1159.

Botner, A. et al., Vet. Rec. 141: 297-499 (1997)

Bosanac, I., Wertz, I. E., Pan, B., Yu, C., Kusam, S., Lam, C., Phu, L., Phung, Q., Maurer, B., Arnott, D., Kirkpatrick, D. S., Dixit, V. M., Hymowitz, S. G., 2010. ubiquitin Binding to A20 ZnF4 Is Required for Modulation of NF-?B Signaling. Molecular Cell 40, 548-557.

Brunger, A. T., 1992. Free R-Value—a Novel Statistical Quantity for Assessing the Accuracy of Crystal-Structures. Nature 355, 472-475.

Capodagli, G. C., McKercher, M. A., Baker, E. A., Masters, E. M., Brunzelle, J. S., Pegan, S. D., 2011. Structural analysis of a viral ovarian tumor domain protease from the Crimean-Congo hemorrhagic fever virus in complex with covalently bonded ubiquitin. J Virol 85, 3621-3630.

Clementz, M. A., Chen, Z., Banach, B. S., Wang, Y., Sun, L., Ratia, K., Baez-Santos, Y. M., Wang, J., Takayama, J., Ghosh, A. K., Li, K., Mesecar, A. D., Baker, S. C., 2010. Deubiquitinating and interferon antagonism activities of coronavirus papain-like proteases. J Virol 84, 4619-4629.

Collaborative Computational Project Number 4, 1994. The CCP4 Suite: Programs for Protein Crystallography. Acta Crystallogr D 50, 760-763.

DeLano, W. L., 2002. The PyMOL Molecular Graphics System. DeLano Scientific, Palo Alto, Calif., USA.

Devaraj, S. G., Wang, N., Chen, Z., Tseng, M., Barretto, N., Lin, R., Peters, C. J., Tseng, C. T., Baker, S. C., Li, K., 2007. Regulation of IRF-3-dependent innate immunity by the papain-like protease domain of the severe acute respiratory syndrome coronavirus. J Biol Chem 282, 32208-32221.

Dikic, I., Wakatsuki, S., Walters, K. J., 2009. Ubiquitin-binding domains—from structures to functions. Nat Rev Mol Cell Biol 10, 659-671.

Dougherty, W. G., Semler, B. L., 1993. Expression of virus-encoded proteinases: functional and structural similarities with cellular enzymes. Microbiol Rev 57, 781-822.

Durfee, L. A., Lyon, N., Seo, K., Huibregtse, J. M., 2010. The ISG15 conjugation system broadly targets newly synthesized proteins: implications for the antiviral function of ISG15. Mol Cell 38, 722-732.

Emsley, P., Cowtan, K., 2004. Coot: model-building tools for molecular graphics. Acta Crystallogr D Biol Crystallogr 60, 2126-2132.

Enesa, K., Zakkar, M., Chaudhury, H., Luong le, A., Rawlinson, L., Mason, J. C., Haskard, D. O., Dean, J. L., Evans, P. C., 2008. NF-kappaB suppression by the deubiquitinating enzyme Cezanne: a novel negative feedback loop in pro-inflammatory signaling. J Biol Chem 283, 7036-7045.

Eswar, N. et al., Comparative Protein Structure Modeling With MODELLER. Current Protocols in Bioinformatics, John Wiley & Sons, Inc., Supplement 15, 5.6.1-5.6.30, 2006.

Fang, Y., Snijder, E. J., 2010. The PRRSV replicase: exploring the multifunctionality of an intriguing set of nonstructural proteins. Virus Res 154, 61-76.

Fitzgerald, K. A., McWhirter, S. M., Faia, K. L., Rowe, D. C., Latz, E., Golenbock, D. T., Coyle, A. J., Liao, S. M., Maniatis, T., 2003. IKKepsilon and TBK1 are essential components of the IRF3 signaling pathway. Nat Immunol 4, 491-496.

Frias-Staheli, N., Giannakopoulos, N. V., Kikkert, M., Taylor, S. L., Bridgen, A., Paragas, J., Richt, J. A., Rowland, R. R., Schmaljohn, C. S., Lenschow, D. J., Snijder, E. J., Garcia-Sastre, A., Virgin, H. W.t., 2007. Ovarian tumor domain-containing viral proteases evade ubiquitin- and ISG15-dependent innate immune responses. Cell Host Microbe 2, 404-416.

Frieman, M., Ratia, K., Johnston, R. E., Mesecar, A. D., Baric, R. S., 2009. Severe acute respiratory syndrome coronavirus papain-like protease ubiquitin-like domain and catalytic domain regulate antagonism of IRF3 and NF-kappaB signaling. J Virol 83, 6689-6705.

Gack, M. U., Albrecht, R. A., Urano, T., Inn, K. S., Huang, I. C., Carnero, E., Farzan, M., Inoue, S., Jung, J. U., Garcia-Sastre, A., 2009. Influenza A virus NS1 targets the ubiquitin ligase TRIM25 to evade recognition by the host viral RNA sensor RIG-I. Cell Host Microbe 5, 439-449.

Gack, M. U., Shin, Y. C., Joo, C. H., Urano, T., Liang, C., Sun, L., Takeuchi, O., Akira, S., Chen, Z., Inoue, S., Jung, J. U., 2007. TRIM25 RING-finger E3 ubiquitin ligase is essential for RIG-1-mediated antiviral activity. Nature 446, 916-920.

Gohara, D. W., Ha, C. S., Kumar, S., Ghosh, B., Arnold, J. J., Wisniewski, T. J., Cameron, C. E., 1999. Production of "authentic" poliovirus RNA-dependent RNA polymerase (3D(pol)) by ubiquitin-protease-mediated cleavage in Escherichia coli. Protein Expr Purif 17, 128-138.

Gorbalenya, A. E., Donchenko, A. P., Blinov, V. M., Koonin, E. V., 1989. Cysteine proteases of positive strand RNA viruses and chymotrypsin-like serine proteases. A distinct protein superfamily with a common structural fold. FEBS letters 243, 103-114.

Gorbalenya, A. E., Koonin, E. V., Lai, M. M., 1991. Putative papain-related thiol proteases of positive-strand RNA viruses. Identification of rubi- and aphthovirus proteases and delineation of a novel conserved domain associated with proteases of rubi-, alpha- and coronaviruses. FEBS letters 288, 201-205.

Hellen, C. U., Krausslich, H. G., Wimmer, E., 1989. Proteolytic processing of polyproteins in the replication of RNA viruses. Biochemistry 28, 9881-9890.

Holm, L., Rosenström, P., 2010. Dali server: conservation mapping in 3D. Nucleic Acids Research 38, W545-W549.

Huang, O. W., Ma, X., Yin, J., Flinders, J., Maurer, T., Kayagaki, N., Phung, Q., Bosanac, I., Arnott, D., Dixit, V. M., Hymowitz, S. G., Starovasnik, M. A., Cochran, A. G., 2012. Phosphorylation-dependent activity of the deubiquitinase DUBA. Nat Struct Mol Biol 19, 171-175.

Inn, K. S., Lee, S. H., Rathbun, J. Y., Wong, L. Y., Toth, Z., Machida, K., Ou, J. H., Jung, J. U., 2011. Inhibition of RIG-1-mediated signaling by Kaposi's sarcoma-associated herpesvirus-encoded deubiquitinase ORF64. J Virol 85, 10899-10904.

James, T. W., Frias-Staheli, N., Bacik, J. P., Levingston Macleod, J. M., Khajehpour, M., Garcia-Sastre, A., Mark, B. L., 2011. Structural basis for the removal of ubiquitin and interferon-stimulated gene 15 by a viral ovarian tumor domain-containing protease. Proc Natl Acad Sci USA 108, 2222-2227.

Jensen, S., Thomsen, A. R., 2012. Sensing of RNA viruses—A review on innate immune receptors involved in recognizing RNA virus invasion. J. Virol.

Jiang, J., Tang, H., 2010. Mechanism of inhibiting type I interferon induction by hepatitis B virus X protein. Protein Cell 1, 1106-1117.

Jiang, X., Chen, Z. J., 2012. The role of ubiquitylation in immune defense and pathogen evasion. Nat Rev Immunol 12, 35-48.

Juang, Y.-C., Landry, M.-C., Sanches, M., Vittal, V., Leung, C. C. Y., Ceccarelli, Derek F., Mateo, A.-Rachele F., Pruneda, Jonathan N., Mao, D. Y. L., Szilard, Rachel K., Orlicky, S., Munro, M., Brzovic, Peter S., Klevit, Rachel E., Sicheri, F., Durocher, D., 2012. OTUB1 Co-opts Lys48-Linked ubiquitin Recognition to Suppress E2 Enzyme Function. Molecular Cell 45, 384-397.

Kamphuis, I. G., Kalk, K. H., Swarte, M. B. A., Drenth, J., 1984. Structure of papain refined at 1.65? resolution. Journal of Molecular Biology 179, 233-256.

Kayagaki, N., Phung, Q., Chan, S., Chaudhari, R., Quan, C., O'Rourke, K. M., Eby, M., Pietras, E., Cheng, G., Bazan, J. F., Zhang, Z., Arnott, D., Dixit, V. M., 2007. DUBA: a deubiquitinase that regulates type I interferon production. Science 318, 1628-1632.

Knoops, K., Barcena, M., Limpens, R. W., Koster, A. J., Mommaas, A. M., Snijder, E. J., 2012. Ultrastructural characterization of arterivirus replication structures: reshaping the endoplasmic reticulum to accommodate viral RNA synthesis. J Virol 86, 2474-2487.

Komander, D., 2009. The emerging complexity of protein ubiquitination. Biochemical Society transactions 37, 937-953.

Komander, D., Clague, M. J., Urbe, S., 2009. Breaking the chains: structure and function of the deubiquitinases. Nat Rev Mol Cell Biol 10, 550-563.

Krausslich, H. G., Nicklin, M. J., Toyoda, H., Etchison, D., Wimmer, E., 1987. Poliovirus proteinase 2A induces cleavage of eucaryotic initiation factor 4F polypeptide p220. J Virol 61, 2711-2718.

Li, S., Zheng, H., Mao, A. P., Zhong, B., Li, Y., Liu, Y., Gao, Y., Ran, Y., Tien, P., Shu, H. B., 2010. Regulation of virus-triggered signaling by OTUB1- and OTUB2-mediated deubiquitination of TRAF3 and TRAF6. J Biol Chem 285, 4291-4297.

Li, X. D., Sun, L., Seth, R. B., Pineda, G., Chen, Z. J., 2005. Hepatitis C virus protease NS3/4A cleaves mitochondrial antiviral signaling protein off the mitochondria to evade innate immunity. Proc Natl Acad Sci USA 102, 17717-17722.

MacLachlan, N. J., Balasuriya, U. B., Hedges, J. F., Schweidler, T. M., McCollum, W. H., Timoney, P. J., Hullinger, P. J., Patton, J. F., 1998. Serologic response of horses to the structural proteins of equine arteritis virus. Journal of veterinary diagnostic investigation: official publication of the American Association of Veterinary Laboratory Diagnosticians, Inc 10, 229-236.

Makarova, K. S., Aravind, L., Koonin, E. V., 2000. A novel superfamily of predicted cysteine proteases from eukaryotes, viruses and *Chlamydia pneumoniae*. Trends Biochem Sci 25, 50-52.

Malakhov, M. P., Kim, K. I., Malakhova, O. A., Jacobs, B. S., Borden, E. C., Zhang, D. E., 2003. High-throughput immunoblotting. Ubiquitin-like protein ISG15 modifies key regulators of signal transduction. J Biol Chem 278, 16608-16613.

Messick, T. E., Russell, N S., Iwata, A. J., Sarachan, K. L., Shiekhattar, R., Shanks, J R., Reyes-Turcu, F. E., Wilkinson, K. D., Marmorstein, R., 2008. Structural basis for ubiquitin recognition by the Otu1 ovarian tumor domain protein. J Biol Chem 283, 11038-11049.

Meylan, E., Curran, J., Hofmann, K., Moradpour, D., Binder, M., Bartenschlager, R., Tschopp, J., 2005. Cardif is an adaptor protein in the RIG-I antiviral pathway and is targeted by hepatitis C virus. Nature 437, 1167-1172.

Nedialkova, D. D., Gorbalenya, A. E., Snijder, E. J., 2010. Arterivirus Nsp1 modulates the accumulation of minus-strand templates to control the relative abundance of viral mRNAs. PLoS Pathog 6, e1000772.

Nielsen, H. S. et al., J. Gen. Virol. 82: 1263-1272 (2001)

O'Neill, L. A., Bowie, A. G., 2010. Sensing and signaling in antiviral innate immunity. Curr Biol 20, R328-333.

Parvatiyar, K., Barber, G. N., Harhaj, E. W., 2010. TAX1BP1 and A20 inhibit antiviral signaling by targeting TBK1-IKKi kinases. J Biol Chem 285, 14999-15009.

Posthuma, C. C., Pedersen, K. W., Lu, Z., Joosten, R. G., Roos, N., Zevenhoven-Dobbe, J. C., Snijder, E. J., 2008. Formation of the arterivirus replication/transcription complex: a key role for nonstructural protein 3 in the remodeling of intracellular membranes. J Virol 82, 4480-4491.

Rui Luo et al., Molec. Immunol. 45: 2839-2846 (2008).

Shembade, N., Ma, A., Harhaj, E. W., 2010. Inhibition of NF-kappaB signaling by A20 through disruption of ubiquitin enzyme complexes. Science 327, 1135-1139.

Snijder, E. J., van Tol, H., Roos, N., Pedersen, K. W., 2001. Non-structural proteins 2 and 3 interact to modify host cell membranes during the formation of the arterivirus replication complex. J Gen Virol 82, 985-994.

Snijder, E. J., Wassenaar, A. L., Spaan, W. J., Gorbalenya, A. E., 1995. The arterivirus Nsp2 protease. An unusual cysteine protease with primary structure similarities to both papain-like and chymotrypsin-like proteases. J Biol Chem 270, 16671-16676.

Storgaard, T. et al., Arch. Virol. 144: 2389-2401 (1999)

Sun, Z., Chen, Z., Lawson, S. R., Fang, Y., 2010. The cysteine protease domain of porcine reproductive and respiratory syndrome virus nonstructural protein 2 possesses deubiquitinating and interferon antagonism functions. J Virol 84, 7832-7846.

Sun, Z., Li, Y., Ransburgh, R., Snijder, E. J., Fang, Y., 2012. Nonstructural protein 2 of porcine reproductive and respiratory syndrome virus inhibits the antiviral function of interferon-stimulated gene 15. J Virol 86, 3839-3850.

van Kasteren, P. B., Beugeling, C., Ninaber, D. K., Frias-Staheli, N., van Boheemen, S., Garcia-Sastre, A., Snijder, E. J., Kikkert, M., 2012. Arterivirus and Nairovirus Ovarian Tumor Domain-Containing Deubiquitinases Target Activated RIG-I To Control Innate Immune Signaling. J Virol 86, 773-785.

Ventoso, I., Carrasco, L., 1995. A poliovirus 2A(pro) mutant unable to cleave 3CD shows inefficient viral protein synthesis and transactivation defects. J Virol 69, 6280-6288.

Versteeg, G. A., Hale, B. G., van Boheemen, S., Wolff, T., Lenschow, D. J., Garcia-Sastre, A., 2010. Species-specific antagonism of host ISGylation by the influenza B virus NS1 protein. J Virol 84, 5423-5430.

Wang, G., Chen, G., Zheng, D., Cheng, G., Tang, H., 2011. PLP2 of mouse hepatitis virus A59 (MHV-A59) targets TBK1 to negatively regulate cellular type I interferon signaling pathway. PLoS One 6, e17192.

Wassenaar, A. L., Spaan, W. J., Gorbalenya, A. E., Snijder, E. J., 1997. Alternative proteolytic processing of the arterivirus replicase ORF1a polyprotein: evidence that NSP2 acts as a cofactor for the NSP4 serine protease. J Virol 71, 9313-9322.

Wiener, R., Zhang, X., Wang, T., Wolberger, C., 2012. The mechanism of OTUB1-mediated inhibition of ubiquitination. Nature 483, 618-622.

Zheng, D., Chen, G., Guo, B., Cheng, G., Tang, H., 2008. PLP2, a potent deubiquitinase from murine hepatitis virus, strongly inhibits cellular type I interferon production. Cell Res 18, 1105-1113.

Ziebuhr, J., Snijder, E. J., Gorbalenya, A. E., 2000. Virus-encoded proteinases and proteolytic processing in the Nidovirales. J Gen Virol 81, 853-879.

The invention claimed is:

1. An Arterivirus that comprises a papain-like protease (PLP2) domain;

wherein said Arterivirus is a live attenuated replication-competent virus selected from the group consisting of an equine arteritis virus (EAV) and a porcine respiratory and reproductive syndrome virus (PRRSV);

wherein said live attenuated replication-competent Arterivirus has a decreased DUB/deISGylating activity due to a mutation in the PLP2 domain of the non-structural protein nsp2; and wherein as depicted for EAV Bucyrus, said mutation in the PLP2 domain is at consensus positions T312, I313, and I353 of the amino acid sequence of SEQ ID NO: 9.

2. A vaccine for the protection of mammals against Arteriviral infection, wherein said vaccine comprises the live attenuated replication-competent Arterivirus of claim 1, and a pharmaceutically acceptable carrier.

3. A method of providing prophylaxis for an Arteriviral infection in a mammal comprising administering the vaccine of claim 2.

4. The vaccine of claim 2, that comprises an additional immunogen of a virus or micro-organism pathogenic to the animal to be vaccinated, an antibody against said immunogen, or genetic information encoding an immunogen of said virus or micro-organism.

5. The vaccine of claim 4, wherein the virus or micro-organism pathogenic to the animal to be vaccinated is selected from the group consisting of Brachyspira hyodysenteriae, African Swine Fever virus, Nipah virus, Porcine Circovirus, Porcine Torque Teno virus, Pseudorabies virus, Porcine influenza virus, Porcine Epidemic Diarrheal virus (PEDV), Foot and Mouth disease virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae*, and *Actinobacillus pleuropneumoniae.*

6. The vaccine of claim 4, wherein the virus or micro-organism pathogenic to the animal to be vaccinated is selected from the group consisting of Equine Influenza virus, *Clostridium tetani*, Equine Herpesvirus 1, and Equine Herpesvirus 4.

* * * * *